(12) United States Patent
Shaw et al.

(10) Patent No.: US 8,999,659 B2
(45) Date of Patent: Apr. 7, 2015

(54) BODY FLUID BIN1 AS A MARKER OF CARDIAC HEALTH

(75) Inventors: Robin Shaw, San Francisco, CA (US); Ting-Ting Hong, San Mateo, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/879,329

(22) PCT Filed: Oct. 20, 2011

(86) PCT No.: PCT/US2011/057155
§ 371 (c)(1),
(2), (4) Date: May 28, 2013

(87) PCT Pub. No.: WO2012/054764
PCT Pub. Date: Apr. 26, 2012

(65) Prior Publication Data
US 2013/0266975 A1 Oct. 10, 2013

Related U.S. Application Data

(60) Provisional application No. 61/405,044, filed on Oct. 20, 2010.

(51) Int. Cl.
*G01N 33/53* (2006.01)
*G01N 33/68* (2006.01)

(52) U.S. Cl.
CPC ........ *G01N 33/6887* (2013.01); *G01N 33/6893* (2013.01); *G01N 2800/325* (2013.01); *G01N 2800/56* (2013.01)

(58) Field of Classification Search
CPC .. C12Q 1/6883; C12Q 1/6886; C12Q 1/6809; C12Q 2600/158; C12Q 2600/112; C12Q 2600/118; C12Q 1/6837; G01N 33/6893; G01N 2500/00; G01N 2800/56; G01N 33/57449; G01N 33/6896; G01N 33/743
See application file for complete search history.

(56) References Cited

U.S. PATENT DOCUMENTS

| 6,410,238 | B1 | 6/2002 | Prendergast et al. | |
| 6,461,828 | B1 | 10/2002 | Stanton et al. | |
| 6,831,063 | B1 * | 12/2004 | Prendergast et al. | 424/94.5 |
| RE39,816 | E | 9/2007 | Stanton et al. | |
| 2004/0106954 | A1 | 6/2004 | Whitehurst et al. | |
| 2004/0241764 | A1 | 12/2004 | Galili | |
| 2006/0263813 | A1 | 11/2006 | Rosenberg et al. | |
| 2010/0092983 | A1 * | 4/2010 | Liew | 435/6 |
| 2011/0008346 | A1 * | 1/2011 | Duckers | 424/136.1 |
| 2012/0094300 | A1 | 4/2012 | Shaw et al. | |

FOREIGN PATENT DOCUMENTS

| WO | WO2007/130549 | * 11/2007 | .......... G01N 33/574 |
| WO | WO20101124240 | * 10/2010 | ............... C12Q 1/68 |
| WO | WO 2012087437 | 6/2012 | |

OTHER PUBLICATIONS

McKenna, Circulation, 1996; 93: 841-842, Report of the 1995 World Health Organization/International Society and Federation of Cardiology Task Force on the Definition and Classification of Cardiomyopathies, whole article).*
LaBaer et al. (Journal of Proteome Research (2005), vol. 4, pp. 1053-1059).*
Mayeux et al. ("Biomarkers: Potential uses and Limitations"; NeuroRx (2004); vol. 1, pp. 182-188).*
Chang, et al. (2007) Bin1 Ablation Increases Susceptibility to Cancer during Aging, Particularly Lung Cancer. *Cancer Res.* 67(16):7605-7612.
Chen, et al. (2002) "L-type Ca2+ channel density and regulation are altered in failing human ventricular myocytes and recover after support with mechanical assist devices" *Circ. Res.* 91(6):517-524.
Cheng, et al. (1993) "Calcium sparks: elementary events underlying excitation-contraction coupling in heart muscle" *Science* 262(5134):740-744.
Dalzell et al. (2009) "Novel Biomarkers in Heart Failure: An Overview" *Biomark Med* 3(5):453-463.
De Groote, et al. (2005) "The impact of beta-adrenoreceptor genepolymorphisms on survival in patients with congestive heart failure" *Eur. J. Heart Fail.* 7(6):966-973.
Dipla, et al. (1998) "Myocyte recovery after mechanical circulatory support in humans with end-stage heart failure" *Circulation* 97:2316-2322.
Doust et al. (2005) "How well does B-type natriuretic peptide predict death and cardiac events in patients with heart failure: systematic review" *BMJ* 330(7492):625, 9 pages.
Etienne-Manneville & Hall (2003) "Cdc42 regulates GSK-3β and adenomatous polyposis coli to control cell polarity" *Nature* 421(6924):753-756.
Fabiato (1983) "Calcium-induced release of calcium from the cardiac sarcoplasmic reticulum" *Am. J. Physiol.* 245(1):C1-C14.
GenBank Accession No. EAW88895 "Calcium channel, voltage-dependent, L type, alpha 1C subunit, isoform CRA_a [*Homo sapiens*]" dated Feb. 4, 2010.
GenBank Accession No. EAW88896 "calcium channel, voltage-dependent, L type, alpha 1C subunit, isoform CRA_b [*Homo sapiens*]"dated Feb. 4, 2010.
GenBank Accession No. EAW88897 "calcium channel, voltage-dependent, L type, alpha 1C subunit, isoform CRA_c [*Homo sapiens*]" dated Feb. 4, 2010.

(Continued)

*Primary Examiner* — Shafiqul Haq
*Assistant Examiner* — Carmencita M Belei
(74) *Attorney, Agent, or Firm* — Shweta Chandra; Carol L. Francis; Bozicevic, Field & Francis LLP

(57) ABSTRACT

The present disclosure provides methods involving use of BIN1 protein levels in biological fluid of a subject in evaluating cardiac health of the subject. The method provided herein may be used to predict a risk of a poor outcome in a subject. The methods also find use in evaluating subjects for assessing patients diagnosed with heart failure. These methods are also useful in assessing therapy options and efficacy of treatment in heart failure patients.

10 Claims, 9 Drawing Sheets

(56) References Cited

OTHER PUBLICATIONS

GenBank Accession No. EAW88898 "calcium channel, voltage-dependent, L type, alpha 1C subunit, isoform CRA_d [*Homo sapiens*]" Feb. 4, 2010.
GenBank Accession No. EAW88899 "calcium channel, voltage-dependent, L type, alpha 1C subunit, isoform CRA_e [*Homo sapiens*]" dated Feb. 4, 2010.
GenBank Accession No. EAW88900 "calcium channel, voltage-dependent, L type, alpha 1C subunit, isoform CRA_f [*Homo sapiens*]" dated Feb. 4, 2010.
GenBank Accession No. EAW88901 "calcium channel, voltage-dependent, L type, alpha 1C subunit, isoform CRA_g [*Homo sapiens*]" dated Feb. 4, 2010.
GenBank Accession No. EAW88902 "calcium channel, voltage-dependent, L type, alpha 1C subunit, isoform CRA_h [*Homo sapiens*]" dated Feb. 4, 2010.
GenBank Accession No. EAW88903 "calcium channel, voltage-dependent, L type, alpha 1C subunit, isoform CRA_i [*Homo sapiens*]" dated Feb. 4, 2010.
GenBank Accession No. EAW88904 "calcium channel, voltage-dependent, L type, alpha 1C subunit, isoform CRA_j [*Homo sapiens*]" dated Feb. 4, 2010.
GenBank Accession No. EAW88905 "calcium channel, voltage-dependent, L type, alpha 1C subunit, isoform CRA_k [*Homo sapiens*]" dated Feb. 4, 2010.
GenBank Accession No. EAW88906 "calcium channel, voltage-dependent, L type, alpha 1C subunit, isoform CRA_l [*Homo sapiens*]" dated Feb. 4, 2010.
GenBank Accession No. EAW88907 "calcium channel, voltage-dependent, L type, alpha 1C subunit, isoform CRA_m [*Homo sapiens*]" dated Feb. 4, 2010.
GenBank Accession No. EAW88908 "calcium channel, voltage-dependent, L type, alpha 1C subunit, isoform CRA_n [*Homo sapiens*]" dated Feb. 4, 2010.
GenBank Accession No. EAW88909 "calcium channel, voltage-dependent, L type, alpha 1C subunit, isoform CRA_o [*Homo sapiens*]" dated Feb. 4, 2010.
GenBank Accession No. EAW88910 "calcium channel, voltage-dependent, L type, alpha 1C subunit, isoform CRA_p [*Homo sapiens*]" dated Feb. 4, 2010.
GenBank Accession No. NM_000719.6 "*Homo sapiens* calcium channel, voltage-dependent, L type, alpha 1C subunit (CACNA1C), transcript variant 18, mRNA" dated Dec. 18, 2011.
GenBank Accession No. NM_004305.2 "*Homo sapiens* bridging integrator 1 (BIN1), transcript variant 8, mRNA" dated Aug. 21, 2011.
GenBank Accession No. NM_139343.1 "*Homo sapiens* bridging integrator 1 (BIN1), transcript variant 1, mRNA" dated Aug. 21, 2011.
GenBank Accession No. NM_139344.1 "*Homo sapiens* bridging integrator 1 (BIN1), transcript variant 2, mRNA" dated Aug. 21, 2011.
GenBank Accession No. NM_139345.1 "*Homo sapiens* bridging integrator 1 (BIN1), transcript variant 3, mRNA" dated Aug. 21, 2011.
GenBank Accession No. NM_139346.1 "*Homo sapiens* bridging integrator 1 (BIN1), transcript variant 4, mRNA" dated Aug. 21, 2011.
GenBank Accession No. NM_139347.1 "*Homo sapiens* bridging integrator 1 (BIN1), transcript variant 5, mRNA" dated Aug. 21, 2011.
GenBank Accession No. NM_139348.1 "*Homo sapiens* bridging integrator 1 (BIN1), transcript variant 6, mRNA" dated Aug. 21, 2011.
GenBank Accession No. NM_139349.1 "*Homo sapiens* bridging integrator 1 (BIN1), transcript variant 7, mRNA" dated Aug. 21, 2011.
GenBank Accession No. NM_139350.1 "*Homo sapiens* bridging integrator 1 (BIN1), transcript variant 9, mRNA" dated Aug. 21, 2011.
GenBank Accession No. NM_139351.1 "*Homo sapiens* bridging integrator 1 (BIN1), transcript variant 10, mRNA" dated Aug. 21, 2011.
GenBank Accession No. NP_000710 "voltage-dependent L-type calcium channel subunit alpha-1C isoform 18 [*Homo sapiens*]" dated Dec. 18, 2011.
Gómez, et al. (1997) "Defective excitation-contraction coupling in experimental cardiac hypertrophy and heart failure" *Science* 276(5313):800-806.
Green, et al. (2005) "APC and EB1 function together in mitosis to regulate spindle dynamics and chromosome alignment" *Mol. Biol. Cell* 16(10):4609-4622.
Gwathmey, et al. (1987) "Abnormal intracellular calcium handling in myocardium from patients with end-stage heart failure" *Circ. Res.* 61(1):70-76.
Hama et al. (1995) "Rapid Ventricular Induction of Brain Natriuretic Peptide Gene Expression in Experimental Acute Myocardial Infarction" *Circulation* 92(6):1558-1564.
Harding, et al. (1994) "Contractile function and response to agonists in myocytes from failing human heart" *Eur. Heart J.* 15(Suppl. D):35-36.
Hasenfuss (1998) "Alterations of calcium-regulatory proteins in heart failure" *Cardiovasc. Res.* 37(2):279-289.
Hasenfuss, et al. (1999) "Relationship between Na+-Ca2+-exchanger protein levels and diastolic function of failing human myocardium" *Circulation* 99(5):641-648.
Hesse, et al. (2007) "Dilated cardiomyopathy is associated with reduced expression of the cardiac sodium channel Scn5a" *Cardiovasc Res.* 75(3):498-509.
Huang et al. (1999) "Cardiac troponin I gene knockout: a mouse model of myocardial troponin I deficiency" *Circ Res* 84(1):1-8.
Hullin, et al. (1999) "Subunit expression of the cardiac L-type calcium channel is differentially regulated in diastolic heart failure of the cardiac allograft" *Circulation* 100(2):155-163.
Hunkeler et al. (1991) "Troponin I isoform expression in human heart" *Circ Res* 69(5):1409-1414.
Inui, et al. (1987) "Isolation of the ryanodine receptor from cardiac sarcoplasmic reticulum and identity with the feet structures" *J. Biol. Chem.* 262(32):15637-15642.
Lee, et al. (2002) "Amphiphysin 2 (Bin1) and T-tubule biogenesis in muscle" *Science* 297(5584):1193-1196.
Lehnart, et al. (2005) "Phosphodiesterase 4D deficiency in the ryanodine-receptor complex promotes heart failure and arrhythmias" *Cell* 123(1):25-35.
Ligon & Holzbaur (2007) "Microtubules tethered at epithelial cell junctions by dynein facilitate efficient junction assembly" *Traffic* 8(7):808-819.
LIMR Link the Newsletter of the Lankenau Institute for Medical Research, Summer 2008. www.limr.org.
Litwin, et al. (2000) "Dyssynchronous Ca(2+) sparks in myocytes from infarcted hearts" *Circ. Res.* 87(11):1040-1047.
Maeda et al. (2000) "High levels of plasma brain natriuretic peptide and interleukin-6 after optimized treatment for heart failure are independent risk factors for morbidity and mortality in patients with congestive heart failure" *J Am Coll Cardiol* 36(5):1587-1593.
Marx, et al. (2000) "PKA phosphorylation dissociates FKBP12.6 from the calcium release channel (ryanodine receptor): defective regulation in failing hearts" *Cell* 101(4):365-376.
Mewes & Ravens (1994) "L-type calcium currents of human myocytes from ventricle of non-failing and failing hearts and from atrium" *J. Mol. Cell. Cardiol.* 26(10):1307-1320.
Missov et al. (1997) "Circulating cardiac troponin I in severe congestive heart failure" *Circulation* 96(9):2953-2958.
Mukherjee et al. (1998) "Changes in L-type calcium channel abundance and function during the transition to pacing-induced congestive heart failure" 37(2):432-444.
Neufeld & White (1997) "Nuclear and cytoplasmic localizations of the adenomatous polyposis coli protein" *Proc. Natl. Acad. Sci. U.S.A.* 94(7):3034-3039.

(56) References Cited

OTHER PUBLICATIONS

Nicot, et al. (2007) Mutations in amphiphysin 2 (BIN1) disrupt interaction with dynamin 2 and cause autosomal recessive centronuclear myopathy. Nature genetics 39, 1134-1139.
Pessah, et al. (1985) "The calcium-ryanodine receptor complex of skeletal and cardiac muscle" *Biochem. Biophys. Res. Commun.* 128(1):449-456.
Piot et al. (1996) "High frequency-induced upregulation of human cardiac calcium currents" *Circulation* 93(1):120-128.
Pollack, et al. (1997) "Dynamics of beta-catenin interactions with APC protein regulate epithelial tubulogenesis" *J. Cell Biol.* 137(7):1651-1662.
Prendergast, et al. (2009) BAR the Door: Cancer Suppression by Amphiphysin-Like Genes. *Biochimica et Biophysica Acta* 1795(1):25-36.
Ricchiuti et al. (1997) "Cardiac troponin I and T alterations in hearts with severe left ventricular remodeling" *Clin Chem* 43(6):990-995.
Schröder, et al. (1998) "Increased availability and open probability of single L-type calcium channels from failing compared with nonfailing human ventricle" *Circulation* 98(10):969-976.
Scriven, et al. (2000) "Distribution of proteins implicated in excitation-contraction coupling in rat ventricular myocytes" *Biophys. J.* 79(5):2682-2691.
Shaw, et al. (2007) "Microtubule plus-end-tracking proteins target gap junctions directly from the cell interior to adherens junctions" *Cell* 128(3):547-560.
Sipido, et al. (1998) "Frequency dependence of Ca2+ release from the sarcoplasmic reticulum in human ventricular myocytes from end-stage heart failure" *Cardiovasc. Res.* 37(2):478-488.
Takahashi, et al. (2004) "Membrane-associated guanylate kinase-like properties of beta-subunits required for modulation of voltage-dependent Ca2+ channels" *Proc. Natl. Acad. Sci. U.S.A.* 101(18):7193-7198.
Tamura et al. (2000) "Cardiac fibrosis in mice lacking brain natriuretic peptide" *Proc Natl Acad Sci USA* 97(8):4239-4244.
Wechsler-Reya, et al. (1998) "A role for the putative tumor suppressor Bin1 in muscle cell differentiation" *Mol. Cell. Biol.* 18(1):566-575.
Westfall & Solaro (1992) "Alterations in myofibrillar function and protein profiles after complete global ischemia in rat hearts" *Circ Res* 70(2):302-313.
Fernando et al. (2009) "Bin1 SRC homology 3 domain acts as a scaffold for myofiber sarcomere assembly" *J Biol Chem* 284(40):27674-27686.
Hong et al. (2010) "BIN1 localizes the L-type calcium channel to cardiac T-tubules" *PLoS Biol* 8(2):e1000312, pp. 1-14.
Muller, et al. (2003) Targeted Disruption of the Murine *Bin1/Amphiphysin II* Gene Does Not Disable Endocytosis but Results in Embryonic Cardiomyopathy with Aberrant Myofibril Formation. *Mol. Cell. Biol.* 23(12):4295-4306.
Sedwick et al. (2010) "Synopsis. BIN1: a protein with great heart" *PLoS Biol* 8(2):e1000311, pp. 1-2.
Hong et al., (2014) "Cardiac BIN1 folds T-tubule membrane, controlling ion flux and limiting arrhythmia", Nature Medicine, 20(6):624-636.
Basso et al. (2009) "Arrhythmogenic right ventricular cardiomyopathy" *Lancet* 373(9671):1289-1300.
GenBank Accession No. NP_004296.1 "myc box-dependent-interacting protein 1 isoform 8 [*Homo sapiens*]" dated Nov. 28, 2011.
GenBank Accession No. NP_647593.1 "myc box-dependent-interacting protein 1 isoform 1 [*Homo sapiens*]" dated Dec. 4, 2011.
GenBank Accession No. NP_647594.1 "myc box-dependent-interacting protein 1 isoform 2 [*Homo sapiens*]" dated Nov. 28, 2011.
GenBank Accession No. NP_647595.1 "myc box-dependent-interacting protein 1 isoform 3 [*Homo sapiens*]" dated Dec. 4, 2011.
GenBank Accession No. NP_647596.1 "myc box-dependent-interacting protein 1 isoform 4 [*Homo sapiens*]" dated Nov. 28, 2011.
GenBank Accession No. NP_647597.1 "myc box-dependent-interacting protein 1 isoform 5 [*Homo sapiens*]" dated Nov. 28, 2011.
GenBank Accession No. NP_647598.1 "myc box-dependent-interacting protein 1 isoform 6 [*Homo sapiens*]" dated Nov. 28, 2011.
GenBank Accession No. NP_647599.1 "myc box-dependent-interacting protein 1 isoform 7 [*Homo sapiens*]" dated Nov. 28, 2011.
GenBank Accession No. NP_647600.1 "myc box-dependent-interacting protein 1 isoform 9 [*Homo sapiens*]" dated Dec. 4, 2011.
GenBank Accession No. NP_647601.1 "myc box-dependent-interacting protein 1 isoform 10 [*Homo sapiens*]" dated Dec. 4, 2011.
Hulot et al. (2004) "Natural history and risk stratification of arrhythmogenic right ventricular dysplasia/cardiomyopathy" *Circulation* 110(14):1879-1884.
Marcus et al. (2010) "Diagnosis of arrhythmogenic right ventricular cardiomyopathy/dysplasia: proposed modification of the task force criteria" *Circulation* 121:1533-1541.
Sen-Chowdhry et al. (2005) "Genetics of right ventricular cardiomyopathy" *J Cardiovasc Electrophysiol* 16(8):927-935.
Barth, et al. (2002) "Dissecting interactions between EB1, microtubules and APC in cortical clusters at the plasma membrane" *J. Cell Sci.* 115(Pt. 8):1583-1590.
Bers (2002) "Cardiac excitation-contraction coupling" *Nature* 415(6868):198-205.
Beuckelmann, et al. (1992) "Intracellular calcium handling in isolated ventricular myocytes from patients with terminal heart failure" *Circulation* 85(3):1046-1055.
Birks, et al. (2006) "Left ventricular assist device and drug therapy for the reversal of heart failure" *N Engl. J Med.* 355(18):1873-1884.
Blaxall et al. (2003) "Differential gene expression and genomic patient stratification following left ventricular assist device support" *J Am Coll Cardiol* 41(7):1096-1106.
Bodor et al. (1997) "Troponin I Phosphorylation in the Normal and Failing Adult Human Heart" *Circulation* 96(5):1495-1500.
Brette & Orchard (2007) "Resurgence of Cardiac T-Tubule Research" *Physiology (Bethesda)* 22:167-173.
Butler, et al. (1997) "Amphiphysin II (SH3P9; BIN1), a member of the amphiphysin/Rvs family, is concentrated in the cortical cytomatrix of axon initial segments and nodes of ranvier in brain and around T tubules in skeletal muscle" *J. Cell Biol.* 137(6):1355-1367.
Chang, et al. (2007) Bin1 Ablation in Mammary Gland Delays Tissue Remodeling and Drives Cancer Progression. *Cancer Res.* 67(1):100-107.

\* cited by examiner

BODY FLUID BIN1 AS A MARKER OF CARDIAC HEALTH

CROSS-REFERENCE TO EARLIER FILED APPLICATION

Pursuant to 35 U.S.C. §119(e), this application claims priority to U.S. Provisional Patent Application Ser. No. 61/405,044, filed Oct. 20, 2010, which application is incorporated herein by reference in its entirety.

STATEMENT REGARDING FEDERALLY SPONSORED RESEARCH

This invention was made with government support under Grant No. HL094414 awarded by the National Institutes of Health (NHLBI). The government has certain rights in the invention.

TECHNICAL FIELD

This invention relates to cardiac health and methods to assess the same.

INTRODUCTION

During the last decade, heart failure has burgeoned into the most prominent public health problem in cardiovascular medicine. Heart failure affects close to 23 million people worldwide and approximately 6 million Americans. The pathophysiology of heart failure, however, is still not well understood and the mortality and economic burden from this disease remains high. Development of cardiac biomarkers have aided in determining diagnosis of acute heart failure as well as that of myocardial infarction.

However, there is a need for a marker that measures the steady-state biochemical health of a heart. There is also a need for a marker that can reliably prognosticate future outcomes for heart failure patients.

SUMMARY

The present disclosure provides methods involving use of BIN1 protein levels in biological fluid of a subject in evaluating cardiac health of the subject. The methods also find use in assessing patients who have heart failure. These methods are also useful in assessing therapy options and efficacy of treatment in heart failure patients and patients who have had heart transplants.

Accordingly, a method for assessing cardiac health of a subject is provided. The method comprises determining a BIN1 protein level in a bodily fluid sample obtained from the subject and using the BIN1 protein level to assess the cardiac health of the subject, where a decreased BIN1 protein level in the bodily fluid sample compared to a normal BIN1 protein level is positively correlated to poor cardiac health. In certain embodiments, the subject may be an individual with a non-acute heart condition. In certain embodiments, the subject may be an individual with risk factors associated with heart failure. In certain embodiments, the subject may be a chronic heart failure patient.

In certain embodiments, BIN1 protein level may be used to determine a cardiac functional classification of the heart failure of a patient with a non-acute heart condition, where the BIN1 protein level is correlated with the cardiac functional classification. In certain embodiments, BIN1 protein level may be used to determine a cardiac functional classification of the heart failure of a chronic heart failure patient, where the BIN1 protein level is correlated with the cardiac functional classification. In certain embodiments, the chronic heart failure patient may be undergoing treatment for heart failure. In certain embodiments, the treatment may comprise use of a mechanical assist device. In certain embodiments, the treatment may comprise a heart transplant. In certain embodiments, the treatment may comprise immunosuppressive therapy.

In certain embodiments, the body fluid sample assayed in the method described herein may comprise a blood sample, a serum sample, or a plasma sample.

Also provided is a method of predicting a risk of poor outcome in a subject, the method comprising determining a BIN1 protein level in a bodily fluid sample obtained from the subject; and using the BIN1 protein level to predict the risk of poor outcome in the subject, wherein a decreased BIN1 protein level in the bodily fluid sample relative to normal BIN1 protein level is correlated to an increased risk of a poor outcome.

In certain embodiments, the subject may be a subject with a no-acute cardiac condition. In certain embodiments, the subject may be a subject diagnosed with chronic heart failure. In certain embodiments, the subject may be undergoing treatment for heart failure. In certain embodiments, the treatment for heart failure may include drug therapy. In certain embodiments, the treatment for heart failure may include a mechanical assist device.

In certain embodiments, the increased risk of a poor outcome may comprise increased risk of heart failure. In certain embodiments, the increased risk of a poor outcome may comprise increased risk of cardiac mortality.

Also disclosed herein is a method of facilitating a diagnosis of an acute cardiac condition, such as a major cardiac event, in a subject, the method comprising determining a BIN1 protein level in a bodily fluid sample obtained from the subject; and using the BIN1 protein level to facilitate a diagnosis of an acute cardiac condition in the subject, wherein an increased BIN1 protein level in the bodily fluid sample relative to normal BIN1 protein level is indicative of an acute cardiac condition. In certain embodiments, the subject may be diagnosed with heart failure. In certain embodiments, the subject may be undergoing treatment for heart failure.

DETAILED DESCRIPTION OF EXEMPLARY EMBODIMENTS

Figure 1A:
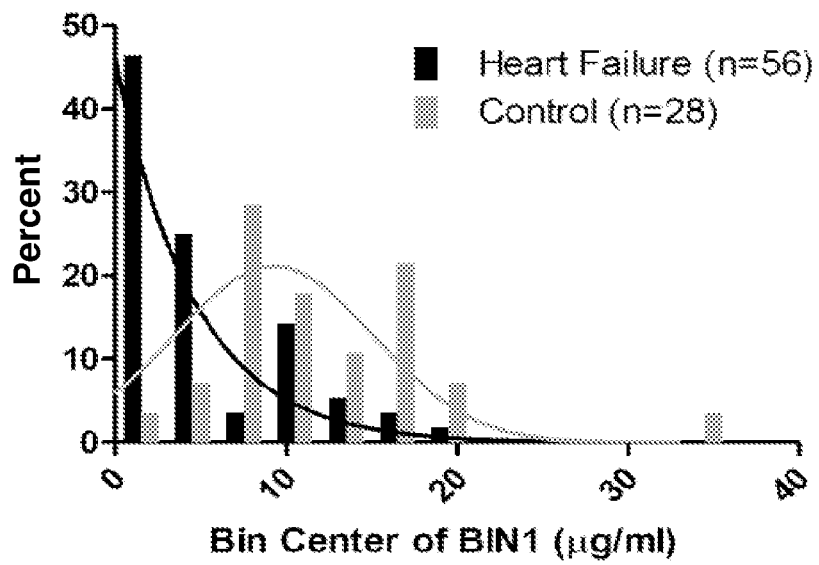
FIGS. 1A and 1B depict the serum BIN1 protein levels in patients with heart failure and in an age matched control group without heart failure.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described. All publications mentioned herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a sample" includes a plurality of such samples and reference to "the sample" includes reference to one or more samples and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "prognosis" as used herein refers to a prediction of likelihood of a particular outcome of a disease in a patient, such as likelihood of survival in a subject with poor heart health, for example, a cardiac disease patient, such as a CHF patient.

The terms "evaluate" and "assess" are used interchangeably herein broadly to refer to facilitating diagnosis and/or prognosis of a condition of interest, and can include assessing the severity of the condition. Accordingly, in the present disclosure, "evaluate" and "assess" can encompass, for example, use of BIN1 protein levels to assess the heart health of a subject, determine a likelihood of a poor clinical outcome (e.g., deterioration of heart health within a selected period of time), and facilitate monitoring of a cardiac condition over a given period of time. For example, BIN 1 protein levels may be used to assess efficacy of a given treatment regimen to improve heart health, and can be used to monitor, predict, or track (i.e., watch or observe), the progression of a cardiac condition in a patient over a period of time.

The terms "body fluid," "bodily fluid," and "biological fluid" are used interchangeably herein, refer to a biological sample of liquid from a subject, for example, a mammal, e.g., from a human. Such fluids include aqueous fluids such as blood (e.g., whole blood or a fraction thereof (e.g., serum, plasma), where the blood may be obtained from any arterial or venous source in the body) and pericardial fluid. Particular bodily fluids that are of interest in the context of the present disclosure include whole blood, serum, plasma, and other blood-derived samples, wherein the term "blood sample" is meant to encompass whole blood or fractions thereof (e.g., serum, plasma). The types of sample can be selected so as to be compatible with the assay format.

"Poor heart health" or "poor cardiac health" as used herein refers to the health of heart of a subject where the heart is functioning at a sub-optimal level compared to the optimal level of function of a normal healthy heart such that the subject may be at risk of developing an acute heart condition such as having a major cardiac event in the future. A heart classified as a heart in poor health is likely to deteriorate in function, for example, develop an acute heart condition, e.g., heart failure exacerbation, without medical intervention or other preventative actions.

"Poor outcome" or "poor cardiac outcome" as used herein in the context of a subject (e.g., a heart failure patient) refers to an outcome associated with declining or poor heart health, such as an acute cardiac condition, e.g., a major cardiac event which can lead to cardiac mortality. "Poor outcome" includes, for example, in a given time period, a failure of left ventricular ejection fraction (LVEF) to improve or the need for mechanical device support (e.g., a left ventricular assist device (LVAD) implant), or the need for a heart transplant, a major cardiac event, or cardiac death.

The phrase "cardiac functional classification" as used herein refers to classifying a heart failure patient on the basis of the functional status of the heart of the heart failure patient. Cardiac functional classification may be an art accepted standard such as the NYHA functional classification, American College of Cardiology/American Heart Association (ACC/AHA) functional classification, for example.

As used herein the term "correlated" is used to refer to a statistical association between two variables which may be a linear or a non-linear association and which may apply across particular ranges of the variables. "Positive correlation" (or "direct correlation") refers to a direct statistical association in between a first variable and a second variable (e.g., a decrease in BIN1 protein level relative to normal BIN1 protein level is statistically associated with a decrease in cardiac health, and an increase in BIN1 protein level relative to normal BIN1 protein level is statistically associated with an increase in cardiac health). "Negative correlation" (or "inverse correlation") refers to an inverse statistical association between a first variable and a second variable (e.g., a decrease in BIN1 protein level relative to normal BIN1 protein level is statistically associated with an increased risk of poor outcome).

The terms "heart failure" (HF) or "congestive heart failure" (CHF), and "congestive cardiac failure" (CCF), are used interchangeably herein, and refer to a clinical condition that may result from any structural or functional cardiac disorder that impairs the ability of the heart to fill with or pump a sufficient amount of blood throughout the body to maintain adequate circulation of blood in the tissues of the body or to pump out the venous blood returned to it by the venous circulation.

The term "end-stage heart failure" refers to CHF that is refractory to conventional medical therapy. Patients with end-stage heart failure have a high mortality rate. These patients frequently undergo multiple frequent hospitalizations, intravenous medications, and require surgical therapies such intraaortic balloon pumps, ventricular assist devices, and heart transplant.

The terms "end-stage dilated cardiomyopathy" and "end-stage CHF" are used interchangeably herein.

The term "cardiomyopathy" or "heart muscle disease" refers to the deterioration of the function of the myocardium (i.e., the heart muscle) for any reason. As used herein, the term "cardiomyopathy" includes "extrinsic cardiomyopathies" and "intrinsic cardiomyopathies". In extrinsic cardiomyopathies the primary pathology is outside the myocardium itself, for example, ischemic cardiomyopathy. In intrinsic cardiomyopathies, weakness in the heart muscle is not due to an identifiable external cause, for example, dilated cardiomyopathy (DCM). In DCM the heart (especially the left ventricle) is enlarged and the pumping function is diminished.

The term "Ischemic cardiomyopathy" refers to cardiomyopathy that results from coronary artery disease, such as atherosclerosis and occlusion of the coronary arteries.

The term "Non-ischemic cardiomyopathy" refers to cardiomyopathy that is not due to coronary artery disease.

The term "cardiac condition" refers to any decrease in function of a heart of a subject. For example, a subject diagnosed with a heart failure, ischemic cardiomyopathy, non-ischemic cardiomyopathy, dilated cardiomyopathy, and the like is diagnosed has having a cardiac condition.

The term "treating" or "treatment" of a condition or disease includes providing a clinical benefit to a subject, and includes: (1) inhibiting the disease, i.e., arresting or reducing the development of the disease or its symptoms, or (2) relieving the disease, i.e., causing regression of the disease or its clinical symptoms.

The terms "individual," "subject," "host," and "patient," are used interchangeably herein and refer to any mammalian subject for whom diagnosis, treatment, or therapy is desired, particularly humans. The mammalian subject may be canine, equine, bovine, or humans.

Overview

The methods of the present disclosure are based on the discovery that BIN1 protein level in body fluid of a subject is useful in assessing cardiac health of the subject and facilitates prediction of risk of poor outcome in a subject as well as diagnosis of an acute cardiac condition.

In general, in a subject who does not have an acute heart condition, decreasing BIN1 protein level in body fluid is positively correlated with declining health of cardiac tissue, and thus with an increasing likelihood of a poor outcome in heart failure patients. For example, as the cardiac health of the subject decreases, the BIN1 protein level in a body fluid sample of the subject decreases relative to a normal BIN1 protein level. For example, as the risk of cardiac mortality in the patient increases, the BIN1 protein level in a body fluid sample of the subject decreases compared to a normal BIN1 protein level. The term "cardiac mortality", as used herein, refers to patient mortality due to cardiac disease. Accordingly, BIN1 protein level in body fluid can be used as a marker of heart health as well as a prognostic marker that is assayed to provide a BIN1 protein level value that decreases as the health of heart tissue decreases.

BIN1 protein level in a body fluid sample is useful in providing a biochemical diagnosis of an acute cardiac condition, e.g., a major cardiac event, an acute heart failure exacerbation or acute coronary syndrome. A significant increase in BIN1 levels in a body fluid of a subject relative to a normal BIN1 protein level is indicative of an acute heart condition.

BIN1 protein levels can be assayed by detection of a BIN1 protein. Exemplary methods for assaying BIN1 protein level are provided below.

The methods of the present disclosure are described in further detail below.

BIN1

Bridging integrator 1 (BIN1) gene encodes a nucleocytosolic protein which was initially identified as a Myc-interacting protein with features of a tumor suppressor. BIN1 is also known as amphiphysin II, amphiphysin-like, and box dependant MYC interacting protein 1. Alternate splicing of the BIN1 gene results in ten transcript variants encoding different isoforms. Some isoforms of BIN1 are expressed ubiquitously while others show a tissue specific expression. BIN1 isoforms 1-7 are expressed in neurons. Isoform 8 is muscle specific while isoforms 9 and 10 are ubiquitous. Isoforms that are expressed in the central nervous system may be involved in synaptic vesicle endocytosis and may interact with dynanim, synaptojanin, endophilin, and clathrin. Aberrant splice variants expressed in tumor cell lines have also been described.

BIN1 expression can be assayed by detection of one or more of the BIN1 isoforms 1-10. BIN1 isoform 1 protein (NP_647593.1), BIN1 isoform 2 protein (NP_647594.1), BIN1 isoform 3 protein (NP_647595.1), BIN1 isoform 4 protein (NP_647596.1), BIN1 isoform 5 protein (NP_647597.1), BIN1 isoform 6 protein (NP_647598.1), BIN1 isoform 7 protein (NP_647599.1), BIN1 isoform 8 protein (NP_004296.1), BIN1 isoform 9 protein (NP_647600.1), and BIN 1 isoform 10 protein (NP_647601.1) sequences are available in the art.

In certain embodiments, BIN1 protein level may be assayed by detection of BIN1 isoform 8 protein. In other embodiments, BIN 1 protein level may be assayed by detection of BIN1 isoform 9 protein. In other embodiments, BIN1 protein level is assayed by detection of both BIN1 isoform 8 protein and BIN1 isoform 9 protein. In exemplary embodiments, BIN1 protein level may be assayed by detection of an amino acid sequence or a structural feature shared by BIN1 isoform 8 protein and BIN1 isoform 9 protein.

In general, BIN1 protein levels may be assayed by using reagents that provide for detection of amino acid sequences and/or structural features shared by various BIN1 isoforms, e.g., by using an antibody that binds an epitope(s) shared by two or more BIN1 isoforms.

Methods for Assaying BIN1 Protein Levels

BIN1 protein levels may be assayed by detecting a BIN1 polypeptide. The levels of BIN1 polypeptide may be detected by an immunodetection assay, such as, quantitative western-blot, immunoprecipation, immunosorbent assay, etc.

In general, BIN1 protein level may be assayed in a sample of body fluid from a patient. The body fluid may be a blood sample, e.g., whole blood, serum, or plasma, for example. The body fluid may be freshly obtained before assaying for BIN1 protein level or may have been stored prior to the assay and/or may have been processed otherwise. The patient sample may be used directly, or diluted as appropriate, usually about 1:10, about 1:100, about 1:500, about 1:1000, about 1:10,000, and usually not more than about 1:50,000. Immunoassays may be performed in any physiological buffer, e.g. phosphate buffered saline, normal saline, etc.

Immunodetection

Immunodetection methods may be suitable for detecting the levels of BIN 1 protein. Thus, antibodies or antisera, such as, polyclonal antisera and monoclonal antibodies specific for BIN1 protein may be used to assess BIN1 protein level. The antibodies can be detected by direct labeling of the antibodies themselves, for example, with radioactive labels, fluorescent labels, hapten labels such as biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. In certain examples, BIN1 protein level in body fluid from a patient may be compared to BIN1 protein level in body fluid of a subject with a normal heart. Immunodetection protocols and kits are well known in the art and are commercially available.

In certain cases, the amount of BIN1 protein present in a body fluid sample may be determined by a western blot. For example, proteins present in a body fluid sample, such as serum, may be separated by SDS-PAGE; the separated proteins transferred to a nitrocellulose membrane; BIN1 detected by using an antibody or antiserum specific for BIN1. At least one normalizing protein, for example, a housekeeping protein such as β-actin may also be detected simultaneously or in parallel and used to normalize the BIN protein levels.

In alternative embodiments, BIN1 polypeptide level may be determined by performing a BIN1 immunoprecipitation using an excess of anti-BIN1 antibody, followed by separation of the immunoprecipitate by SDS-PAGE; the separated proteins transferred to a nitrocellulose membrane; and detected by staining the gel, e.g., by Coommassie Blue or silver staining. Immunoprecipitation of a control protein such as ubiquitin may also be carried out either simultaneously or in parallel. Optionally, the same procedure may be carried out on corresponding body fluid from a normal subject.

In certain cases, an immunosorbent assay (for example, an enzyme linked immunosorbent assay (ELISA)) may be used to detect BIN1 protein levels. In general, a solid support is first reacted with a solid phase component (e.g., BIN1 protein, or an anti-BIN1 antibody) under suitable binding conditions such that the component is sufficiently immobilized to the support. Optionally, immobilization of the solid phase component to the support can be enhanced by first coupling the solid phase component to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, biotin, avidin, streptavidin, and the like. Such molecules and methods of coupling these molecules to the solid phase component, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After contacting the solid support with the solid phase component, any non-immobilized solid-phase components are removed from the support by washing. Before adding the biological sample or a fraction thereof, the non-specific binding sites on the insoluble support, i.e., those not occupied by a target peptide, are generally blocked. Preferred blocking agents include non-interfering proteins such as bovine serum albumin, casein, gelatin, and the like. Several detergents at non-interfering concentrations, such as Tween, NP40, TX100, and the like may be used.

In the embodiments where the support-bound solid phase component is a BIN1 binding moiety, for example, an anti-BIN1 antibody, the bound solid phase component is then contacted under suitable binding conditions with the biological sample being assayed. After washing, a solution containing a secondary binder moiety is added under suitable binding conditions, wherein the secondary binder is capable of associating selectively with the BIN1 bound to the BIN1 binding moiety. A BIN1 binding moiety may be selected from an anti-BIN1 antibody, a BIN1 binding protein (e.g., Cav1.2), for example.

In the embodiments where the support-bound solid phase component is BIN1 polypeptide present in a body fluid sample, the bound solid phase component is then contacted under suitable binding conditions with a BIN1 binding moiety, for example, an anti-BIN1 antibody. After washing, a solution containing a secondary binder moiety is added under suitable binding conditions, wherein the secondary binder is capable of associating selectively with the BIN1 binding moiety.

The presence of the secondary binder can then be detected using techniques well known in the art. In a certain embodiments, the solution containing a secondary binder moiety is a solution containing a secondary antibody that binds to an anti-BIN1 antibody. The secondary antibody may be in the form of monoclonal or polyclonal sera, e.g. mouse anti-human antibodies, goat anti-human antibodies, rabbit anti-human antibodies, etc.

Secondary antibodies may be labeled to facilitate direct or indirect detection and/or quantification of binding. Examples of labels which permit direct measurement of secondary binder moiety binding include radiolabels, such as $^3$H or $^{125}$I, fluorescent moieties, dyes, beads, chemilumnescent moieties, electrochemilumnescent moieties, colloidal particles, and the like. Useful labels include fluorochromes, e.g. Cy2, Cy3, Cy5, fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA)). Examples of labels that permit indirect measurement of binding include enzymes where the substrate may provide for a colored or fluorescent product. In a certain embodiment, the secondary antibody is labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Alternatively, the secondary antibody may be unlabeled, and a labeled tertiary antibody may be used. Since the resultant signal is thus amplified, this technique may be advantageous where only a small amount of BIN1 is present.

After the secondary antibody has bound, the insoluble support is generally again washed free of non-specifically bound molecules, and the signal produced by the bound conjugate is detected by conventional means. Where an enzyme conjugate is used, an appropriate enzyme substrate is provided so a detectable product is formed. More specifically, where a peroxidase is the selected enzyme conjugate, a substrate combination is $H_2O_2$ and is O-phenylenediamine, which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490-495 nm is conveniently measured with a spectrophotometer.

Generally the amount of BIN1 protein detected will be compared to control samples from normal subjects, or to a known normal range or level of BIN1 present in body fluid of subjects with healthy heart, or to a known BIN1 protein level range present in heart failure patients with a poor outcome, or with known BIN1 protein level range present in heart failure patients without a poor outcome.

An immunosorbent assay, such as a sandwich ELISA assay format, can be used, wherein a solid support (e.g., a well of a microtiter plate) is coated with a BIN1-binding moiety, such as an anti-BIN1 antibody. A biological sample to be assayed is then added to the coated wells. Optionally, a series of standards, containing known concentrations of the BIN1 protein can be assayed in parallel with the samples or aliquots thereof to serve as controls.

Generally from about 0.001 to 1 ml of sample, diluted or otherwise, is sufficient. Dilution of the sample where necessary can be done in buffers (such as Tris, PBS, and the like) to stabilize pH to 5-10, optionally also containing surfactants such as Tween 20 and non-specific background blocking protein or serum components, such as bovine serum albumin or rabbit serum. Furthermore, in certain embodiments, each sample and standard, if used, will be added to multiple wells so that mean values can be obtained for each. The test and control samples are each incubated with the solid support for a time sufficient for binding of an antibody to antigen to occur. Generally, from about 0.1 to 3 hr is sufficient, usually 1 hr sufficing.

After a period of incubation sufficient to allow antibody binding to the target antigen, the support(s) can be washed to remove unbound antigen. Generally, a dilute non-ionic detergent medium at an appropriate pH, generally 7-8, is used as a wash medium. An isotonic buffer, such as phosphate-buffered saline, may be employed in the washing step. From one to six washes may be employed, with sufficient volume to thoroughly wash non-specifically bound proteins present in the sample. Preferably, the washing step will not cause dissociation of the BIN1 polypeptide bound to the coated BIN1-binding moiety. Following the wash, a detectably labeled secondary binding molecule is added. The second binding molecule may be a BIN1 binding moiety, for example, anti-BIN1 antibody. The secondary binding molecule is allowed to react with any captured BIN1, the support is washed and the presence of the secondary binding molecule detected using methods well known in the art.

In such assays, the concentration of the second antibody will generally be about 0.1 to 50 μg/ml, preferably about 1 μg/ml. The solution containing the second antibody is generally buffered in the range of about pH 6.5-9.5. The incubation time should be sufficient for the second antibody to bind available molecules. Generally, from about 0.1 to 3 hours is sufficient, usually 1 hour sufficing. After the second antibody has bound, the insoluble support is generally again washed free of non-specifically bound material, essentially as described for prior washes. After non-specifically bound material has been cleared, the signal produced by the bound conjugate is detected by conventional means.

Solid supports which can be used in the subject methods include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

The solid support may be blocked with a protein, such as bovine serum albumin, or the body fluid sample may be incubated with the solid support in the presence of a blocking protein.

Meso Scale Discovery® Assays

The methods for determining the level of BIN1 protein in a body fluid sample may be carried out in an assay format that uses Meso Scale Discovery® (MSD) platform. In general, a secondary binder moiety that is conjugated to an electrochemiluminescent label is used and detection of electrochemiluminescence from secondary binder moiety is utilized in the MSD platform.

The MSD technology involves uses of MULTI-ARRAY® and MULTI-SPOT® microplates with electrodes integrated into the bottom of the plate. Electrochemiluminescence detection uses labels that emit light when electrochemically stimulated. Background signals are minimal because the stimulation mechanism (electricity) is decoupled from the signal (light). Labels are stable and may be coupled to secondary binder moieties via a variety of coupling chemistries. They emit light at about 620 nm, eliminating problems with color quenching. Multiple excitation cycles of each label may be used to amplify the signal to enhance light levels and improve sensitivity. The detection process is initiated at electrodes located in the bottom of MSD's microplates. Labels sufficiently near the electrode are excited and detected, enabling non-washed assays. MSD Read Buffers contain coreactants that enhance the electrochemiluminescence signals.

A first molecule may be bound to a MSD microplate by direct binding to the microplate by passive absorption. The second molecule bound to the first molecule may be detected by electrically stimulating an electrochemiluminescent tag which may be attached to the second molecule directly or indirectly via a third molecule. Thus, a first BIN1 binding moiety may be bound to the plate by passive absorption; incubated with a sample of interest and BIN1 in the sample bound to the BIN1 binding moiety. The bound BIN1 detected by a second BIN1 binding moiety, which may be detected by using an electrochemiluminescent tagged-antibody specific for the second BIN1 binding moiety.

Alternatively, a first molecule may immobilized on a precoated MSD microplate. The MSD microplate may be precoated with avidin or streptavidin, for example, and a first molecule conjugated to biotin. The binding of a second molecule to the immobilized first molecule may be detected as above.

Alternatively, a complex containing a first and a second molecule may be immobilized on the microplate and detected as described above.

SECTOR instruments may be used for the electrical stimulation of the electrochemiluminescent tag and for measuring the signal generated from the stimulation of the tag.

Electrochemiluminescent tags include MSD-TAG™, such as, sulfo-tags, as well as, other electrochemiluminescent tags compatible with the MSD assay platform.

Samples

A biological fluid sample can be any sample in which BIN1 protein may be present. As noted above, biological samples of liquid from a mammal, e.g., from a human may be assayed to detect BIN1 protein levels. Such fluids include aqueous fluids such as blood (e.g., whole blood or a fraction thereof (e.g., serum, plasma)), pericardial fluid, and the like.

Particular bodily fluids that are of interest include whole blood, serum, plasma, and other blood-derived samples. The term "blood sample" is meant to encompass whole blood or fractions thereof (e.g., serum, plasma). The types of sample can be selected so as to be compatible with the assay format.

The sample volume can be any volume that is compatible with the specific assay format. In some embodiments, the sample will be diluted in a suitable solution prior to assaying for the levels of BIN1 polypeptide. In general, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, Tween-20 and the like.

Appropriate control samples for the assay include body fluid sample, e.g., blood sample collected from subjects who are diagnosed has not having heart failure (i.e. a normal heart), or samples which contain a known, predetermined amount of BIN1 (i.e., a positive control). An example of a positive control may be cell lysate of a cell line expressing BIN1 protein. In these cases, the control samples provide an assurance that the assay has been performed correctly and the reagents are stable when the expected results are obtained from the controls.

In many embodiments, a suitable initial source for the body fluid sample is a blood sample. As such, the sample employed in the subject assays is generally a blood-derived sample. The blood sample may be derived form whole blood or a fraction thereof, e.g., serum, plasma, etc., where in some embodiments the sample is derived from blood that is allowed to clot and the serum separated and collected to be used in BIN1 detection assay.

In embodiments in which the sample is a serum or serum derived sample, the sample is generally a fluid sample. Any convenient methodology for producing a fluid serum sample may be employed. In many embodiments, the method employs drawing venous blood by skin puncture (e.g., finger stick, venipuncture) into a clotting or serum separator tube, allowing the blood to clot, and centrifuging the serum away from the clotted blood. The serum is then collected and stored until assayed. In some cases, blood may be collected from a subject by venipuncture. 0.1-0.5 ml may be used to prepare serum or plasma. Serum may be prepared just after blood drawing. Tubes may be left at room temperature for 4 hours following centrifugation after which serum is removed.

Serum may be aliquoted and stored at −20° C. Plasma may be prepared by adding EDTA (final concentration of 5 mM) to a blood sample. Blood sample may be centrifuged, supernatant removed and stored at −20° C. Once the patient derived sample is obtained, the sample is assayed to determine the level of BIN1.

The sample may be treated in a variety of ways so as to enhance detection of the level of BIN1. For example, where the sample is blood, the red blood cells may be removed from the sample (e.g., by centrifugation) prior to assaying. Detection of the presence of BIN1 may also be enhanced by concentrating the sample using procedures well known in the art (e.g. acid precipitation, alcohol precipitation, salt precipitation, hydrophobic precipitation, filtration (using a filter which is capable of retaining molecules greater than 30 kD, e.g. Centrim 30™), affinity purification). In certain cases, certain types of proteins may be depleted from the sample before the assay is performed.

Use of BIN1 Protein Levels in Assessing Heart Health and Prognosis of Risk of Cardiac Mortality BIN1 protein levels in body fluid of a subject can be used to assess the cardiac health of a subject and/or determine the risk of a poor clinical outcome. BIN1 protein levels can also be used to facilitate a diagnosis of an acute cardiac condition (e.g., myocardial infarction). Assessing cardiac health may include predicting the risk of a poor outcome in a subject, for example, a subject who has been clinically diagnosed as having heart failure.

In general, BIN1 protein levels in a body fluid (e.g., blood) lower than a normal BIN1 protein level are indicative of declining heart health in the subject, and can facilitate an assessment of the subject's cardiac health and/or a provide a prognosis of the likelihood of poor outcome. A decreased BIN1 protein level in a body fluid compared to a normal BIN1 protein level is positively correlated to a decrease in cardiac health or poor cardiac health. Decreased BIN1 protein levels relative to a normal BIN1 protein level is correlated with an increase in the risk of a poor outcome, such as, acute heart condition, cardiac mortality, ventricular arrhythmia, and the like in the future.

However, where BIN1 protein levels in a body fluid are significantly higher than a normal BIN1 protein level, such facilitates a diagnosis of an acute cardiac condition or a major cardiac event, such as a myocardial infarction.

Thus, BIN1 protein levels find use not only in assessing cardiac health, providing a prognosis of outcome, and facilitating diagnosis of an acute cardiac condition, such as, a major cardiac event, BIN1 protein levels also provide a marker to differentiate subjects having a major cardiac event from those that do not have a major cardiac event n.

The uses of the BIN1 protein levels are described below in more detail.

Use of BIN1 Protein Levels

The method can involve assaying a BIN1 protein level in a body fluid sample from a subject, for example, an individual having an acute cardiac condition, such as a major cardiac event, an individual not having an acute cardiac condition, e.g., having a non-acute cardiac condition, or non-evident cardiac condition.

Analysis of BIN1 protein level can involve comparison of the BIN protein level to a normal BIN1 protein level. The normal BIN1 protein level may be a BIN1 protein level known to be indicative of a healthy heart. A normal BIN1 protein level generally refers to a BIN1 protein level in a body fluid sample from a subject with a non-failing heart. A normal BIN1 protein level can be determined from BIN1 protein levels in body fluid sample obtained from an individual whose heart function was deduced to be normal from an examination of the gross morphology of the heart, left ventricular ejection fraction, cardiac catheterization, and/or from lack of heart related condition in the individual medical record, and the like. A normal BIN1 protein level can be determined from BIN1 protein level in a pooled body fluid sample obtained by combining body fluid samples obtained from multiple individuals whose heart function was deduced to be normal. Accordingly, a normal BIN1 protein level may be the BIN1 protein level in a pooled body fluid sample obtained by combining body fluid samples obtained from multiple individuals whose heart function was deduced to be normal.

Analysis of BIN1 protein level can involve normalization of BIN1 protein level to BIN1 protein level in a pooled sample of body fluid samples from healthy individuals.

Determining BIN1 protein level to assess cardiac health and/or provide a prognosis of outcome, or facilitate diagnosis of an acute cardiac condition in a subject may further involve determining levels of one or more serological markers of heart failure, e.g., B-type Natriuretic Peptide (BNP), and/or Creatine kinase (CK), and/or CK-MB; and/or troponin (specifically, cardiac troponin T and cardiac troponin I). The assaying of serological markers of heart failure may be performed before, after, or simultaneously with assaying BIN1 protein levels in a body fluid sample of a subject.

Determining BIN1 protein level to assess cardiac health and/or provide a prognosis of outcome, or facilitate diagnosis of an acute cardiac condition in a subject may be performed in conjunction with other physical assessments usually performed to diagnose heart health, for example, screening for physical symptoms, such as, swelling in the ankles, sudden weight gain from water retention, decreased ability to exercise, chest pain, nausea, dizziness, etc.

In certain embodiments, determining BIN1 protein level to assess cardiac health and/or provide a prognosis of outcome, or facilitate diagnosis of an acute cardiac condition in a subject may further involve determining levels of one or more serological markers of heart failure and/or performing physical assessment of the subject.

Use of BIN1 Protein Levels in Subjects to Facilitate Diagnosis of Heart Health and/or Facilitate Prognosis of Outcome BIN1 protein levels in a body fluid (e.g., blood) are useful to facilitate diagnosis of heart health and/or facilitate prognosis of outcome. Decreased BIN 1 protein levels in a body fluid (e.g., blood) of a subject relative to a normal BIN1 protein level are indicative of declining heart health in the subject. Decreased BIN1 protein levels in a body fluid (e.g., blood) of a subject relative to a normal BIN1 protein level can facilitate an assessment of the subject's cardiac health and/or a provide a prognosis of the likelihood of poor outcome. The subject may be a subject with a non-evident cardiac condition or a non-acute cardiac condition, for example, a subject not having a major cardiac event.

A significantly low BIN1 protein level in a body fluid sample of a subject compared to a normal BIN1 protein level indicates that the patient has a poor cardiac health. A significantly low BIN1 protein level in a body fluid sample of a subject compared to a normal BIN1 protein level is correlated to an increased likelihood of a poor outcome. In contrast, a BIN1 protein level close to the normal value indicates that the subject has a good heart health or in case of a heart failure patient, a decreased likelihood of a poor outcome, e.g., an acute cardiac condition, or cardiac mortality.

A low BIN1 protein level compared to a normal BIN1 protein level indicates that the subject has poor heart health and predicts an increased likelihood of poor outcome, e.g., an acute cardiac condition, cardiac mortality, ventricular arrhythmia. In general, at least a 20% reduction in BIN1 protein level compared to a normal BIN level is a significant decrease and indicates that a subject has poor heart health. For example, a 20% or more reduction, or a 30% or more reduction, or a 40% or more reduction, or a 45% or more reduction, or a 50% or more reduction, or a 55% or more reduction, or a 60% or more reduction, or a 65% or more reduction, or a 70% or more reduction, or a 75% or more reduction, or a 80% or more reduction, or a 85% or more reduction, or a 90% reduction, or more, in BIN1 protein level compared to a normal BIN level indicates that a subject has poor heart health. For a CHF patient at least a 25% reduction in BIN1 protein level compared to a normal BIN level indicates an increased likelihood of cardiac mortality.

In general, a patient with at least a 25% reduction, for example, a 30% reduction, a 40% reduction, a 50% reduction, a 75% reduction, or more, in BIN1 protein level compared to a normal BIN level (or a normal range) has an increased risk of poor outcome.

BIN 1 protein levels may be used to predict the risk of a poor outcome over a period of time following the assessment of the BIN1 protein level, for example, the risk of a poor outcome for the CHF patient over the next 3 months-60 months, e.g., 6 months-18 months, such as, over the next 6 months-12 months, or 12 months-18 months, or 18 months-24 months, 24 months-30 months, or 30 months-36 months, or 36 months to 42 months, or 36 months to 48 months, or 24 months to 54 months, or 24 months to 60 months, or longer.

BIN1 protein levels for a patient can also be assessed relative to a threshold value. A "threshold value" or "risk threshold value" is a value selected so as to facilitate distinguishing among relative outcome, e.g., to facilitate distinguishing between a relatively high risk of poor outcome from a relatively low risk of a poor outcome. For example, in most cases the threshold value is an approximate value below which risk of a poor outcome is relatively higher, and above which risk of a poor outcome is relatively lower.

In certain cases, there may be two threshold values, a first threshold value and a second threshold value. For example, BIN 1 protein levels below the first threshold value but above the second threshold value may indicate that the subject has poor heart health but not a high risk of poor outcome at the time point at which the assessment was performed. BIN1 protein levels below the second threshold value may indicate that the subject has poor heart health and a high risk of poor outcome, such as an acute cardiac condition, cardiac mortality.

For example, a BIN1 protein level of about 30% less than the normal BIN1 protein level represents a first threshold value and a BIN1 protein level of about 50% less than the normal BIN1 protein level represents a second threshold value. A subject having a BIN protein level lower than the first threshold value have a poor heart health relative to a subject having a BIN1 protein level greater than or equal to this threshold value. A subject having a BIN1 protein level lower than the first threshold value but higher than the second threshold value have a poor heart health but a decreased risk of poor outcome. A subject having a BIN1 protein level lower than the second threshold value have a relatively increased risk of a poor outcome, and cardiac patients having a BIN1 protein level greater than or equal to this threshold value have a relatively decreased risk of poor outcome.

BIN1 protein levels can also be used to stratify heart failure patients between different functional classes. In general, heart failure patients with BIN1 protein level within a first range (for example, between about 60% to 45% of the normal BIN1 protein level) may be classified into a higher functional class (for example, NYHA Class 1 or Class 2) while heart failure patients with BIN1 protein level within a second range (for example between about 40% to 0% of the normal BIN1 protein level) may be classified into a lower functional class (for example, NYHA Class 3 or Class 4). Heart failure patients with BIN1 protein level within the second range (for example between about 40% to 0% of the normal BIN1 protein level) classified into a lower functional class may be further stratified between Class 3 and 4 with patients having BIN1 protein levels below about 20% of the normal BIN1 protein level classified as Class 4 while patients having BIN1 protein levels above about 20% of the normal BIN1 protein level but below about 40% of the normal BIN1 protein level classified as Class 3 patients.

BIN1 protein levels may be used to predict the risk of a poor outcome over a period of time following assessment, for example, the risk of a poor outcome for the CHF patient over the next 5 years, e.g., 3 months-60 months, such as, over the next 6 months-12 months, or 12 months-18 months or 18 months-24 months, 24 months-30 months, or 30 months-36 months, or 36 months to 42 months, or 36 months to 48 months, or 24 months to 54 months, or 24 months to 60 months, or longer.

BIN1 protein level may be used to diagnose arrhythmogenic right ventricular cardiomyopathy (ARVC) in a subject. In addition, BIN1 protein level may be used to diagnose disease severity and/or predict disease progression in a subject diagnosed with ARVC. In general, a decreased BIN1 protein level in body fluid of a patient, diagnosed with ARVC, relative to a normal BIN1 level is correlated to an increased severity of ARVC and predicts a higher risk of a poor outcome, such as, further progression of ARVC and/or future arrhythmia, for example. Thus, BIN1 protein level may be used in a method for assessing cardiac health of a subject diagnosed with ARVC. The method may include determining a BIN1 protein level in a bodily fluid sample obtained from the subject diagnosed with ARVC and using the BIN1 protein level to assess the cardiac health of the subject, wherein a decreased BIN1 protein level in the bodily fluid sample compared to a normal BIN1 protein level is positively correlated to the severity of ARVC.

BIN1 protein level may be used in a method of predicting a risk of poor outcome such as further progression of ARVC and/or future arrhythmia event in a subject diagnosed with ARVC. The method may include determining a BIN1 protein level in a bodily fluid sample obtained from the subject diagnosed with ARVC; and using the BIN1 protein level to predict the risk of poor outcome in the subject, wherein a decreased BIN1 protein level in the bodily fluid sample relative to normal BIN1 protein level is correlated to an increased risk of a poor outcome, such as, progression of ARVC into severe ARVC and/or occurrence of arrhythmia event(s) in the future.

Use of BIN1 Protein Levels to Facilitate a Diagnosis of an Acute Heart Condition Determining a BIN1 protein level in a body fluid sample of a subject is useful in facilitating a diagnosis of an acute cardiac condition, such as, a major cardiac event. In general, a significantly increased BIN1 protein level in a body fluid relative to a normal BIN1 protein level is indicative of a major cardiac event in the subject. Thus, body fluid BIN1 protein level is useful as a marker for differentiating subjects having an acute cardiac condition, such as, a major cardiac event from those that do not have an acute cardiac condition. Such assays can facilitate a differential diagnosis in subjects otherwise exhibiting symptoms of a major cardiac event. Accordingly, in a subject exhibiting symptoms of a major cardiac event, the occurrence of a major cardiac event can be diagnosed if the BIN1 protein level in a body fluid of the subject is significantly increased relative to a normal BIN1 protein level. On the other hand, absence of a significantly increased BIN1 protein level relative to a normal BIN1 protein level indicates that the subject is not having a major cardiac event.

An acute cardiac condition or a major cardiac event may include acute coronary syndrome, myocardial infarction, or acute fulminant myocarditis.

A significantly high body fluid BIN1 protein level compared to a normal BIN1 protein level indicates that the subject has an acute cardiac condition. In general, at least a 20% increase in BIN1 protein level compared to a normal BIN level is significant and indicates that a subject has an acute cardiac condition, such as, a major cardiac event. For example, a patient with a 20% increase, a 30% increase, a 40% increase, a 50% increase, a 75% increase, or more, in BIN1 protein level compared to a normal BIN level (or a normal range) has an acute cardiac condition.

Subjects

In general, subjects amenable to methods described herein are mammalian subject, for example canine, bovine, equine, or human subjects.

Subjects without Acute Heart Condition

Subjects amenable to evaluation using the methods of the present disclosure include subjects who do not have an acute heart condition, for example, subjects with non-evident heart condition, subjects with non-acute, but chronic, heart condition, and the like.

The terms "non-evident heart condition" or "non-evident cardiac condition" as used herein refer to a subject having a decrease in heart function that is not yet clinically evident in the subject. Subjects having a "non-evident heart condition" include, for example, a patient in early stages of compromised heart who does not yet exhibit clear clinical symptoms. Such subjects may include individuals that may be predisposed to heart related health problems, for example, individuals with a family history of heart related problems, for example, close relatives who have suffered from cardiac events; individuals that suffer from obesity, and/or hypertension, and/or high cholesterol, and the like; individuals who have suffered from a cardiac condition in the past.

A subject whose body fluid level of BIN 1 may be determined to assess cardiac health of the subject may include an individual who presents symptoms that may indicate that the individual has a cardiac condition, for example, an individual who presents with chest pain, dizziness, shortness of breadth, nausea, sweating, etc.

A subject whose body fluid level of BIN1 may be determined to assess cardiac health of the subject may include an individual who is diagnosed as having a non-acute heart condition. The terms "non-acute heart condition" or "non-acute cardiac condition" as used herein refer to a subject exhibiting clinical symptoms associated with a heart condition, but which heart condition is not acute, e.g., arrhythmogenic right ventricular cardiomyopathy (ARVC), chronic heart failure, chronic progressive non-ischemic cardiomyopathy, or chronic progressive ischemic cardiomyopathy. Subjects with a non-acute heart condition generally are not hospitalized for treatment of the cardiac condition and can be managed as cardiac out-patients.

Subjects with Acute Heart Condition

Subjects amenable to evaluation using the methods of the present disclosure include subjects who have an acute heart condition. The terms "acute heart condition" or "acute cardiac condition" as used herein refers to a subject exhibiting clinical symptoms associated with a heart condition, which symptoms are of greater severity than clinical symptoms exhibited by a subject having a non-acute heart condition. Subjects with an acute heart condition are usually hospitalized for the heart condition and under constant monitoring, or sometimes can be managed with very frequent out-patient clinical supervision. "Acute heart conditions" include a major cardiac event, such as, acute coronary syndrome, myocardial infarction, or acute fulminant myocarditis. A subject with an acute heart condition may have other serologic evidence of an acute heart condition, e.g., has higher than normal levels of B-type Natriuretic Peptide (BNP), has higher than normal levels of Creatine kinase (CK), has higher than normal levels of CK-MB, or has higher than normal levels of troponin (specifically, cardiac troponin T and cardiac troponin I). In certain cases, a subject with an acute heart condition may have more than one of the above mentioned indications.

Clinical Applications

BIN1 protein levels in a body fluid sample of a subject are useful in facilitating cardiac health assessment, predicting risk of a poor outcome, and also for diagnosing an acute heart condition, such as, a major cardiac event. In certain embodiments, BIN1 protein levels are used in conjunction with other indicators of cardiac disease to facilitate cardiac health assessment, predicting risk of a poor outcome, and for diagnosing an acute heart condition.

Subjects with Non-Acute Heart Condition

Determination of BIN1 protein level in body fluid sample from a non-acute heart condition patient may be used to assign functional class to a patient, for example, a New York Heart Association (NYHA) Class 1-4, as discussed above. This functional classification may be used to determine a priority level to the patient for receiving a heart transplant. Determination of BIN1 protein level in body fluid sample from a non-acute heart condition patient may be used to facilitate assessing response to CHF treatment, and/or to guide modification of a treatment plan.

In general, in the case of patients with non-acute heart condition, the lower the BIN1 protein level compared to normal BIN1 protein level, the higher the likelihood of poor cardiac recovery and hence the patient is assigned a high priority level for receiving a heart transplant. Alternatively, if a non-acute heart condition patient has a near normal BIN level, the expectation is that the heart has a good chance to recover, and the patient might be assigned a low priority level for receiving a heart transplant. In general, the lower the BIN1 protein level compared to normal BIN1 protein level, the higher is the priority level of the patient for receiving a heart transplant.

Similarly, in patients with only moderately decreased BIN1 compared to normal BIN1 protein level, there would be increased priority of placing the patient on a left ventricular assist device to help the patient recover. Removal of the left ventricular assist device could be timed with recovery of BIN level to a normal or near normal level.

BIN1 protein levels may be used to determine the risk of cardiac mortality. In general, the lower the BIN1 protein level, the higher is the risk of cardiac mortality. For example, in certain cases a BIN1 protein level of 40% or less than the normal BIN1 protein level, for example, 30% or less, or 20% or less than the normal BIN1 protein level predicts cardiac mortality within 5 years in absence of appropriate medical intervention. Appropriate medical intervention may include heart transplant, LVAD, and the like.

A determination of a risk of a poor outcome, e.g., an acute cardiac condition, cardiac mortality, may be used to assess efficacy of CHF treatment and to determine a change to treatment strategy. A CHF patient may be undergoing treatment by, for example, surgery, mechanical assist device, biventricular pacer, heart transplant, and drug therapy. The efficacy of a CHF treatment may be assessed by assaying for BIN1 level. In general, a low BIN1 compared to normal BIN1 protein level indicates a high likelihood of a cardiac failure and that the treatment is not efficacious. Such a determination of treatment efficacy may be used to alter the treatment. For example, by classifying the patient at a high priority level for a heart transplant.

On the other hand, a CHF treatment may stabilize the BIN level resulting in a normal or near normal level, for example above a threshold level. As a failing heart recovers, the BIN1 protein level becomes normal or close to normal BIN1 protein level. A normal BIN1 protein level indicates a decreased likelihood of a cardiac failure and that the treatment is efficacious. This information may be used to classify the patient at a low priority level for receiving a heart transplant, and can indicate other therapies such as an intraortic balloon pump, ventricular assist device, intravenous heart therapy.

A BIN1 protein level may be used to determine therapy options. For example, a BIN1 protein level less than about 40% of normal BIN1 protein level may be correlated to an increased risk of a poor outcome. A BIN1 protein level of less than about 40% or less, 30% or less, 20% or less than normal BIN1 protein level may be positively correlated to a poor outcome for the patient in the near future, for example, in the next 3 months-60 months, e.g., 3 month-6 months, 6 months-8 months, 8 months-12 months, 12 months-18 months, 18 months-24 months, 18 months to 30 months, 18 months-46 months, 18 months to 60 months. The poor outcome may be death, LVAD implant, or no improvement in LVEF or even a further deterioration of LVEF. This information may be used to classify the patient at a high priority level for receiving a heart transplant, and can indicate other therapies such as an intraortic balloon pump, ventricular assist device, intravenous heart therapy.

Subjects with Acute Heart Condition

Assessing BIN1 protein levels in a body fluid sample of a subject suspected of having an acute heart condition finds use in facilitating a diagnosis of an acute heart condition, such as, a major cardiac event. Providing a diagnosis of acute heart condition may include assessing a BIN1 protein level in a body fluid of a subject, as described above, in conjunction with assessing a protein level of a known marker of an acute heart condition, e.g., BNP, CK, CK-MB, and/or troponin. The phrase "in conjunction" includes assessing BIN1 protein levels and another marker of acute heart condition sequentially or simultaneously. Providing a diagnosis of an acute heart condition in a subject suspected of having an acute heart condition can facilitate determining treatment protocol(s) for the subject.

Kits

The materials for use in the methods of the present disclosure are suited for preparation of kits produced in accordance with well known procedures. The present disclosure thus provides kits comprising agents, which may be BIN1 binding moiety (or moieties) for quantitating the level of BIN1 for predicting clinical outcome, determining treatment options or predicting response to treatment, etc. In addition, the kits may optionally comprise the reagent(s) with an identifying description or label or instructions relating to their use in the methods of the present disclosure. The kits may comprise containers (including microtiter plates suitable for use in an automated implementation of the method), each with one or more of the various reagents (typically in concentrated form) utilized in the methods, including, for example, pre-fabricated microarrays, buffers, antibodies, enzyme substrates, and the like of the present disclosure. Mathematical algorithms used to estimate or quantify prognostic and/or predictive information are also properly potential components of kits.

The methods provided by the present disclosure may also be automated in whole or in part.

Reports

The methods of the present disclosure are suited for the preparation of reports summarizing the results of assaying the level of BIN 1. In certain embodiments, a report may include a determination of the cardiac health of a subject. In certain embodiments, a report may include a determination of the risk of cardiac mortality in a CHF patient. A "report," as described herein, is an electronic or tangible document which includes report elements that provide information of interest relating to BIN1 protein level in a body fluid sample of a subject and/or a risk of cardiac mortality. The report can be completely or partially electronically generated, e.g., presented on an electronic display (e.g., computer monitor). A report can further include one or more of: 1) information regarding the testing facility; 2) service provider information; 3) patient data; 4) sample data; 5) an interpretive report, which can include various information including: a) indication; b) test data, and 6) other features.

The present disclosure thus provides for methods of creating reports and the reports resulting therefrom. The report may include a summary of the levels of the BIN1 in the body fluid sample obtained from the patient. The report may include an assessment of risk of cardiac mortality. The report may include a recommendation for treatment modality such as surgery alone or surgery in combination with therapy. The report may be presented in electronic format or on paper. The methods disclosed herein can further include a step of generating or outputting a report, which report can be provided in the form of an electronic medium (e.g., an electronic display on a computer monitor), or in the form of a tangible medium (e.g., a report printed on paper or other tangible medium).

For clarity, it should be noted that the term "user," which is used interchangeably with "client," is meant to refer to a person or entity to whom a report is transmitted, and may be the same person or entity who does one or more of the following: a) collects a sample; b) processes a sample; c) provides a sample or a processed sample; and d) generates data for use in the risk of cardiac mortality assessment, for example. In some cases, the person(s) or entity(ies) who provides sample collection and/or sample processing and/or data generation, and the person who receives the results and/or report may be different persons, but are both referred to as "users" or "clients" herein to avoid confusion. In certain embodiments, e.g., where the methods are completely executed on a single computer, the user or client provides for data input and review of data output. A "user" can be a health professional (e.g., a clinician, a laboratory technician, a physician (e.g., a cardiologist, surgeon, primary care physician), etc.).

In embodiments where the user only executes a portion of the method, the individual who, after computerized data processing according to the methods of the invention, reviews data output (e.g., results prior to release to provide a complete report, a complete report, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Where government regulations or other restrictions apply (e.g., requirements by health, malpractice, or liability insurance), all results, whether generated wholly or partially electronically, are subjected to a quality control routine prior to release to the user.

Computer-Based Systems and Methods

The methods and systems described herein can be implemented in numerous ways. In one embodiment of particular interest, the methods involve use of a communications infrastructure, for example the interne. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility). In some embodiments, the step of using the BIN1 protein level to determine the risk of cardiac mortality in a CHF patient is performed by a computer programmed to execute an algorithm for calculating the risk. In other examples, the subject method includes causing a computer to execute an algorithm for calculating the risk of cardiac mortality in a CHF patient based on the level of BIN1.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., level of a BIN1 protein, and a BNP protein level; and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or interne). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh, etc.), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present disclosure.

Where used, the database(s) is usually connected to the database server component and can be any device which will hold data. For example, the database can be a magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc., as desired.

Computer-Readable Storage Media

The present disclosure also contemplates a computer-readable storage medium (e.g. CD-ROM, memory key, flash memory card, diskette, etc.) having stored thereon a program which, when executed in a computing environment, provides for implementation of algorithms to carry out all or a portion of the calculation of risk of cardiac mortality, as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained. The computer-readable storage medium can also be provided in combination with one or more reagents for carrying out the assaying step of the subject method (e.g., primers, probes, arrays, or other such kit components).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Centigrade.

Materials and Methods

BIN1 ELISA Assay.

BIN1 ELISA assay was designed using a commercial ELISA reagent set (BD Bioscience). Briefly, 96-well plate was plated with a capture antibody mouse anti-BIN1 (1:1000, Sigma) at 4° C. overnight. Following washing and blocking with dilution buffer for 1 hour at room temperature, both standards and samples were added and incubated for 1 hour with rotation at room temperature to allow for BIN1 capture. Following a series of washes, primary goat anti-BIN1 antibody (1:1000, Abcam) was then added to detect the captured BIN 1 protein. After thorough washes, bound primary goat anti-BIN1 was detected by incubation with a HRP conjugated donkey anti-goat IgG secondary antibody (1:4000, Abcam). Finally, after washes, substrate TMB was added for an hour and reaction was terminated by stop buffer. The optical density of each well was read immediately at 405 nm wavelength using a microplate reader (BioRad).

BIN1 standards were generated from lysates of 293FT cells overexpressing exogenous BIN1. The BIN1 concentration in the standards was referred to the total protein concentration in the lysates. A standard curve ($R^2 > 0.98$) was generated from standards ranging from 0.04 ng/µl to 20 ng/µl. For serum samples, a total amount of 100 µl of serum samples were loaded into each well. The amount of BIN1 was generated from the standard curve and expressed as ng/µl.

Cardiac output was determined during an invasive right heart catheterization performed in the cardiac catheterization laboratory. A balloon-tipped pulmonary artery catheter is inserted into the venous system, advanced to the right atrium, then right ventricle, then pulmonary artery. Cardiac output is then obtained by both the thermodilution technique. (which consists of injecting cold saline through a proximal port and recording the temperature change at the distal port for an estimation of output) or the more commonly used Fick technique which consists of dividing the estimated oxygen consumption by the arterial-venous oxygen gradient obtained from the hematocrit and arterial and mixed venous oxygen saturation.

Example 1

Serum BIN1 Protein Levels in Healthy Subjects and Subjects with Heart Failure

Figure 1B:
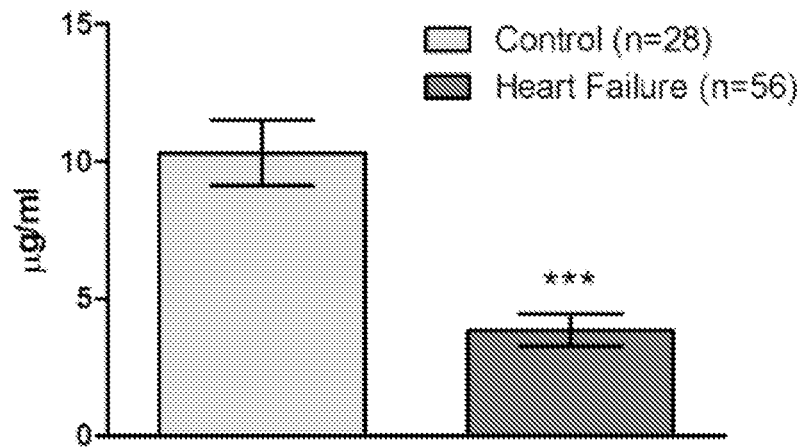

Serum BIN1 protein levels in 56 patients diagnosed with heart failure and 28 age matched healthy individuals measured (Control group). Serum samples were obtained from heart failure patients at UCSF Advanced Heart Failure and Transplant clinic. BIN1 protein levels were measured by an ELISA assay and are shown in FIGS. 1A and 1B. FIG. 1A depicts BIN1 Frequency Distribution as measured as BIN1 protein level and the percent of heart failure patients and controls showing a particular BIN protein level. As is seen in FIG. 1A, a greater percent of the heart failure patients had a lower level of serum BIN1 as compared to the control individuals whose serum BIN1 protein level centered around about 9 µg/ml. FIG. 1B provides the mean serum BIN 1 level of the control individuals and the heart failure patients.

FIGS. 1A and 1B. Serum Bin1 in Heart Failure Clinic is Different from Control. FIG. 1A. Histogram of serum BIN1 protein levels of heart failure patients at UCSF Advanced Heart Failure and Transplant clinic (black bars) and age-matched controls (grey bars). Note frequency distribution in heart failure patients is shifted to the left of the normal serum BIN1. FIG. 1B. Mean serum BIN1 protein level of control patients (gray) which is about one third of heart failure patients. (*** $p < 0.005$).

The data indicate that BIN1 in failing hearts in less than half that of patients without heart failure (control group).

Example 2

BIN1 Protein Level does not Correlate with Gender, Age, Weight, or Body Mass Index (BMI)

Serum BIN1 protein measured in heart failure patients were plotted relative to age, gender, weight, and BMI of the patients. No correlation of the serum BIN1 protein levels to age, gender, weight, or BMI was apparent.

Figure 2A:
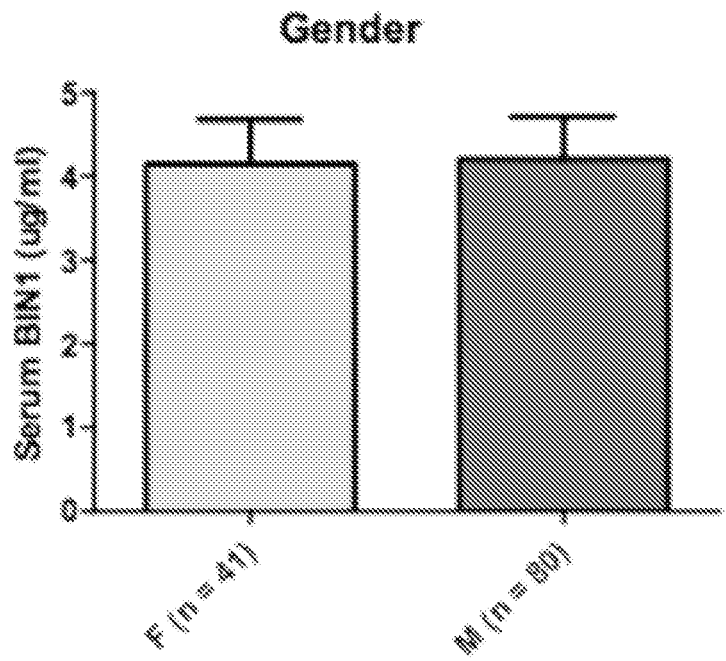
FIGS. 2A and 2B show that serum BIN1 protein level does not correlate with gender (FIG. 2A) or with age (FIG. 2B).
Figure 2B:
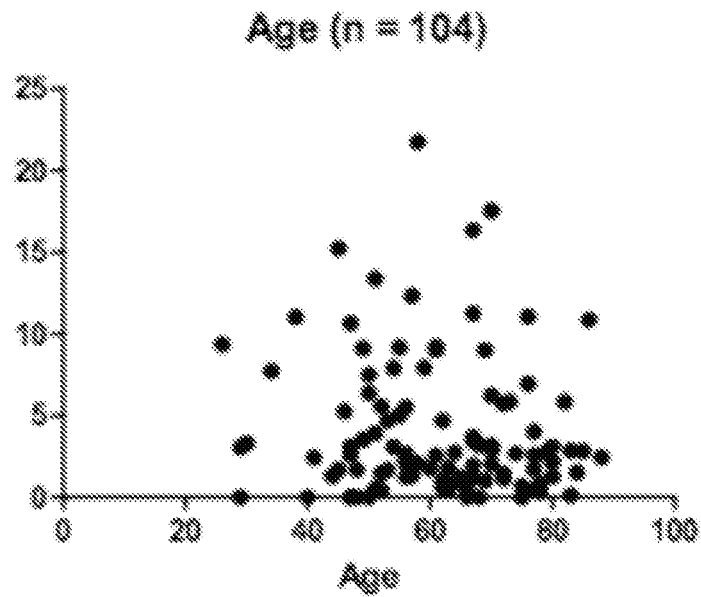

FIGS. 2A and 2B. Serum BIN1 does not correlate with sex and age. Within the patients studied, there is no significant difference in BIN1 protein levels in male versus female patients (FIG. 2A) and with age (FIG. 2B).

Figure 3A:
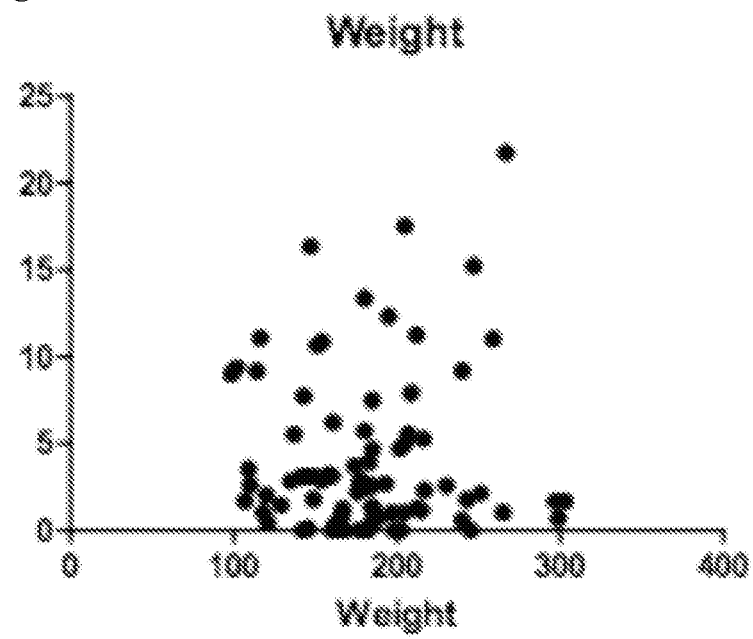
FIGS. 3A and 3B show that serum BIN1 protein level does not correlate with weight (FIG. 3A) or with body mass index (BMI) (FIG. 3B).
Figure 3B:
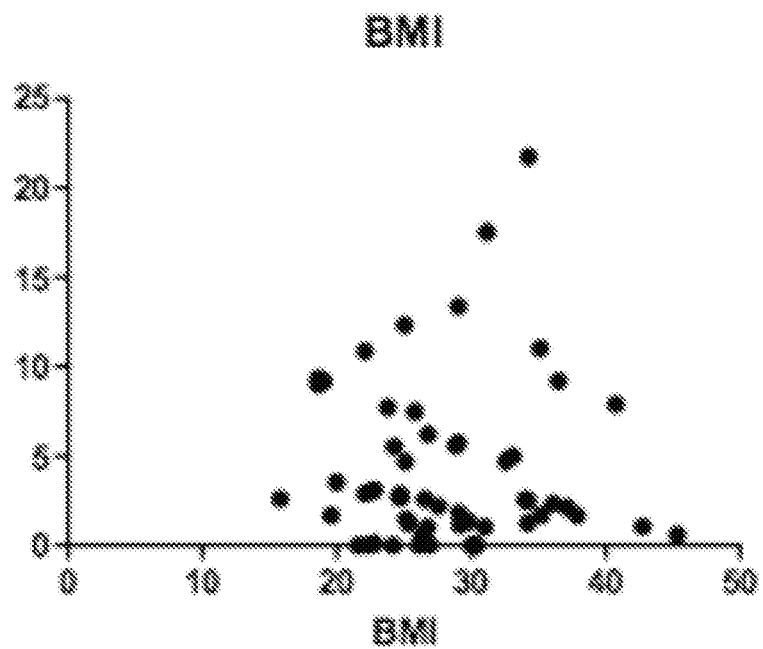

FIGS. 3A and 3B. Serum BIN1 does not correlate with weight and BMI. Within the patients studied, there is no significant difference in BIN1 protein levels when evaluated against weight (in pounds) or Body Mass Index (weight in kilograms divided by the square of height in meters).

Example 3

BIN1 Protein Level does not Correlate with Pulmonary Capillary Wedge Pressure

Figure 4A:
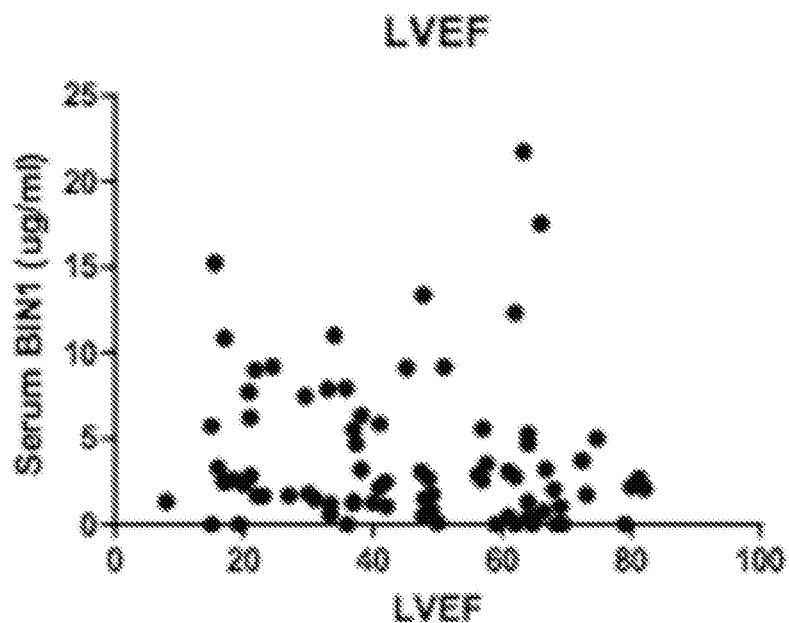
FIGS. 4A and 4B show that serum BIN1 protein level does not correlate with left ventricular ejection fraction (LVEF) (FIG. 4A) or with pulmonary capillary wedge pressure (PCWP) (FIG. 4B).
Figure 4B:
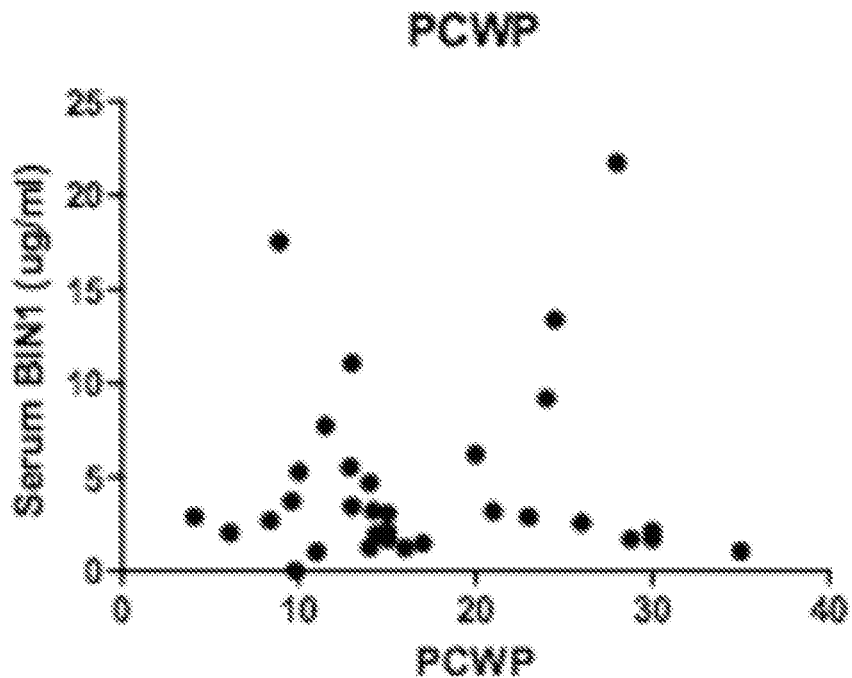

Within the heart failure patients studied, left ventricular ejection fraction (LVEF) were obtained by echocardiogram, and invasive right heart catheterization hemodynamics were performed to measure pulmonary capillary wedge pressure (PCWP). There is no significant difference in BIN1 protein levels and these two parameters (FIGS. 4A and 4B). Note that PCWP is a measure of intracardiac filling pressure which is reflected by the serum marker BNP.

Example 4

BIN1 Protein Level Correlates with Cardiac Output and Cardiac Index

Figures 5A, 5B:
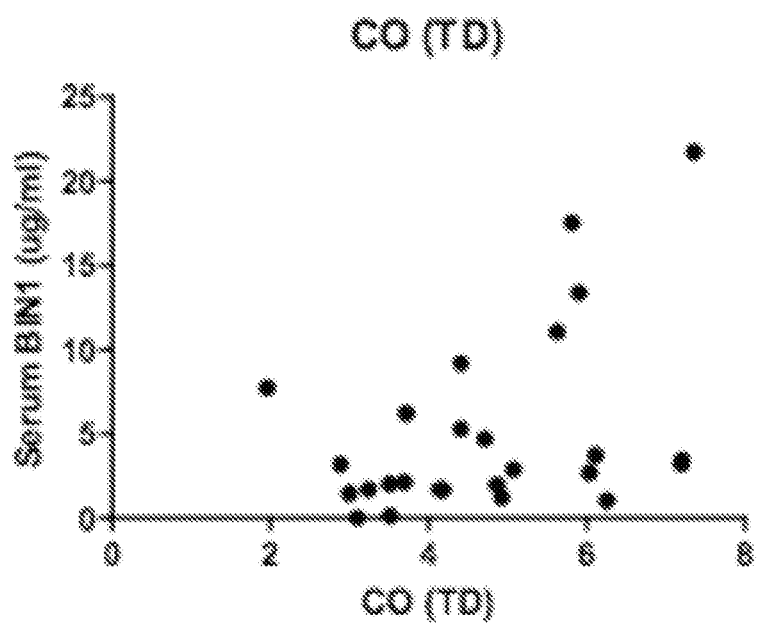
FIGS. 5A and 5B depicts that serum BIN1 correlates with cardiac output (CO) (FIG. 5A) and with cardiac index (CI) (FIG. 5B).

FIGS. 5A and 5B indicates that serum BIN1 does directly correlate with invasively determined cardiac output and cardiac index. The lower the serum BIN1, the lower the cardiac output. This is a significant marker because serum BIN1 is much less invasive than pulmonary artery catheter determined cardiac output.

FIGS. 5A and 5B. Serum Bin1 correlates with cardiac output. There is a roughly linear relationship between BIN1 and invasively measured (by Fick equation) cardiac output in liters/minutes, and cardiac index which is cardiac output divided by estimated body surface area (in meters squared).

Example 5

BIN1 Protein Level Correlates with New York Heart Association (NYHA) Functional Class NYHA functional class was determined by expert heart failure cardiologists in UCSF Advanced Heart Failure and Transplant Clinic. BIN1 was plotted after being binned by patient function status, as defined by class I, II, III, and IV on the NYHA scale. NYHA scale was obtained from patients' clinic note at the time blood sample was drawn for determining BIN1 protein level. Increasing class indicates worsening symptoms. Class 4 (or IV) encompasses patients who are symptomatic at rest. Prognosis on these patients is extremely poor.

Figure 6:
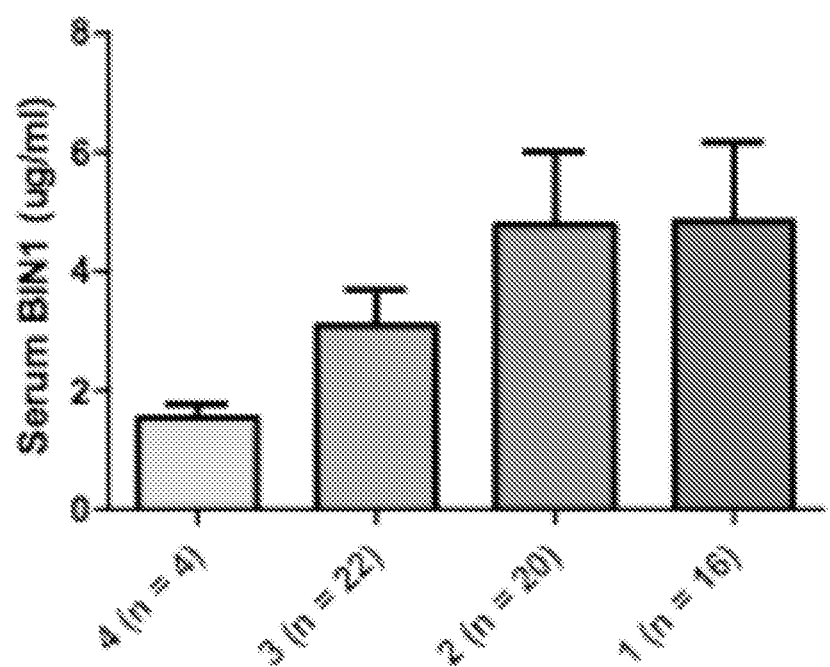
FIG. 6 shows that serum BIN1 correlates with New York Heart Association (NYHA) functional class (Class 1-Class 4).

As shown in FIG. 6, there is a strong correlation between serum BIN1 protein level and the NYHA functional class.

Lower levels of BIN1 correlate with the NYHA class 4 while relatively higher level of BIN correlates with NYHA class 1 or 2. The first column (leftmost column) is NYHA Class IV, the next column is Class III, the next column is Class II, and the last column (rightmost column) is Class I.

The strong correlation with serum BIN1 protein level indicates that functional class now may be tested and quantified by blood test independent of a subjective physical examination.

Example 6

BIN1 Protein Level Correlates with Mortality

Figure 7A:
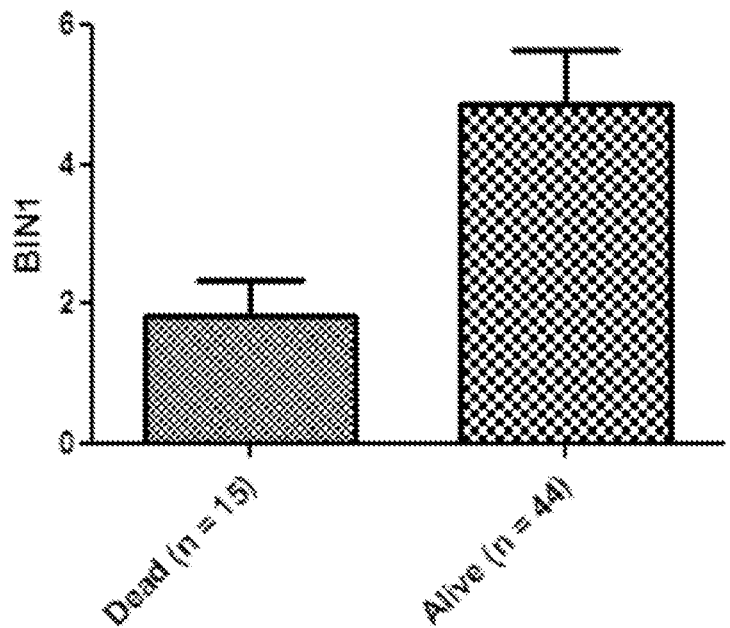
FIGS. 7A and 7B depicts that low serum BIN1 correlates with a higher risk of mortality.
Figure 7B:
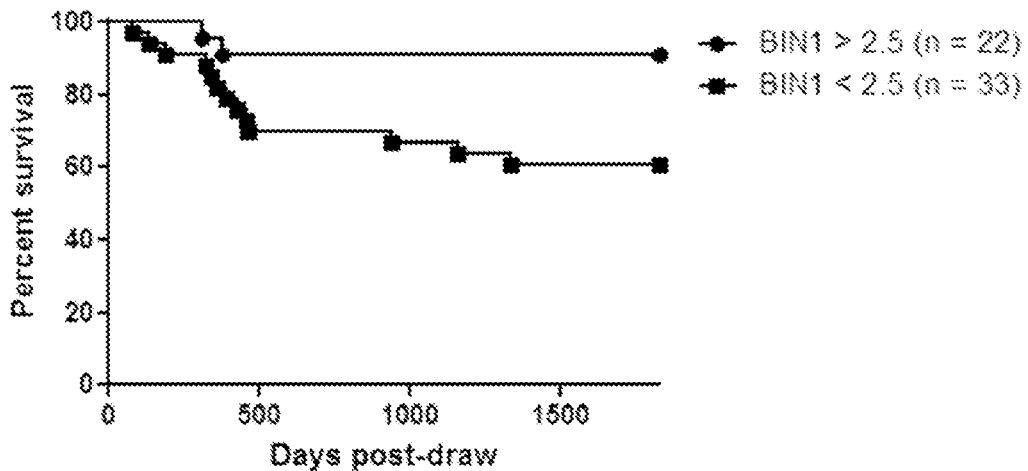

Heart failure patients whose BIN1 protein level was evaluated were followed up in a retrospective study over a period of five years. FIGS. 7A and 7B illustrates that there is a high rate of mortality in patients with a low BIN1 protein level. The converse is that patients with a higher BIN1 were likely to be alive in that same period of time. These data indicates the usefulness of BIN1 protein levels for a serum based prognostication for patients with heart failure. Patients with a BIN1 of five and higher will likely not need a transplant or other advanced therapy such as left ventricular assist device in the upcoming five years. Those with a low BIN1 will need such therapy. Note that a BIN1 of five is still 50% of normal (FIG. 1A or 1B). Thus BIN1 should be able to stratify the general heart failure population.

FIG. 7A. Serum Bin1 correlates with mortality. In patients with whom follow-up is available five years after serum draw, average BIN1 protein levels are binned between those who are dead (left bar) and those who are alive (right bar). Low Bin1 predicts a significantly increased risk of death in the next five years.

FIG. 7B. Serum BIN1 predicts mortality. Kaplan-Meier survival curve of heart failure patients who has a serum BIN1 protein level of less that 2.5 versus those greater than or equal to 2.5. Over a five year period, patients with Bin1<2.5 have a significantly less chance of survival.

Example 7

BIN1 Protein Level Correlates with Disease Severity and Predict Future Arrhythmia Events in Patients with ARVC ARVC is a disease characterized by focal or diffuse fibro-fatty replacement of the ventricular myocardium, which can result in recurrent ventricular arrhythmias and right and/or left ventricular dysfunction (Basso C. et al., Lancet 2009; 373: 1289-300). The disease is familial and several causative genes involved in desmosome function have been implicated (Sen-Chowdhry S., et al., J Cardiovasc Electrophysiol 2005; 16: 927-35). Disease severity and progression can range from asymptomatic disease to severe heart failure and refractory ventricular arrhythmias (Hulot J S, et al., Circulation 2004; 110: 1879-84). Currently, it is difficult to predict future arrhythmia burden in ARVC patients or which of the patients will develop progressive heart failure. A test to identify individuals at high risk of clinical progression would be of considerable clinical utility.

Methods

Patients.

The study was approved by the institutional review boards of the hospitals of University of California San Francisco (UCSF) and Johns Hopkins University (Western IRB, with clinical data collected via a Johns Hopkins protocol). All participating patients gave informed consent. Venous blood sample was collected over a period of about seven years from thirty one patients diagnosed with ARVC). Seven patients had two blood samples drawn at separate time points. Blood samples were obtained and centrifuged at 4000 rpm for 20 minutes at 4° C., and plasma stored in −80° C. freezer for later ELISA analysis. Corresponding clinical data for each patient including MRI, RV angiogram, right heart catheterization, echocardiogram, pathology, ECG, signal averaged ECG, Holter monitor results, family history and genotype were recorded for confirmation of ARVC diagnosis.

Patients were included in the study if a diagnosis of ARVC could be confirmed with available data according to the modified International Task Force Criteria (Marcus F. I., et al. Circulation 2010; 121: 1533-41) by two separate cardiologists blinded to the assay results. Exclusion criteria included inadequate data to confirm diagnosis or presence of ventricular tachycardia (VT) storm or several defibrillation events at the time of the blood draw, which might be expected to cause spurious BIN1 measurement.

Of the initial 31 patients with a possible diagnosis of ARVC, 24 were included in the final analysis. Three patients were excluded based on incomplete data and two for failure to meet diagnostic criteria. Two patients with active VT storm and several defibrillation events at the time of the lab draw were also excluded. The patient characteristics are displayed in Table 1.

A control group consisted of 48 age, sex, and BMI-matched healthy controls without diabetes, hypertension or history of cardiac disease. These controls were identified from a large UCSF database containing clinical data and plasma specimens from healthy volunteers. All participants gave consent to future use of these specimens.

Measurement of Plasma BIN1.

A commercial ELISA reagent set (BD Bioscience, San Diego, Calif.) was used to design a highly-sensitive ELISA test to quantify BIN1 in human plasma. This assay system uses two antibodies against human BIN1. A mouse monoclonal anti-BIN1 (1:500 in coating buffer, Sigma, St. Louis, Mo.) was used as the capture antibody and a primary goat anti-BIN1 antibody (1:500 in 1% BSA, Everest, Clifton, N.J.) was used as the detection antibody. BIN1 standards were generated from lysates of 293FT cells overexpressing exogenous human BIN1. A standard curve ($R^2$>0.98) was generated to determine the relative amount of BIN1 in each sample. The determined plasma concentration of BIN1 of each individual was normalized to and expressed as percent of BIN1 value in plasma pooled from three 25 year-old healthy male adults. This assay is highly reproducible with an intra-assay variability of <5%. Plasma BIN1 levels were then measured in duplicate from all ARVC and control samples. For patients with serial blood draws, the earliest sample draw was used for the cross-sectional analysis.

Measurement of Baseline Characteristics and Future Arrhythmia Events in ARVC Patients.

All clinical data were obtained by persons blinded to the BIN1 assay results. Baseline New York Heart Association (NYHA) class, RV and LV function, and ventricular arrhythmia history were recorded for each patient. NYHA class was obtained from chart review, RV and LV function were determined by echocardiography, and ventricular arrhythmia history was obtained from chart review and ICD (implantable cardioverter-defibrillator) interrogation data. For the quantitative arrhythmia analysis, ventricular arrhythmia events were weighted as follows: history of sudden cardiac death or sustained ventricular tachycardia (VT) was counted as one event, appropriate ICD therapy for sustained VT or ventricular fibrillation (VF) was counted as one event (even if several therapies were required for termination), and hospitalization for persistent VT or VT storm was weighted as 1.5 events. For the prospective analysis, all arrhythmia events from baseline plasma draw to date of last follow up were recorded. For patients with serial draws, NYHA class, interval arrhythmia history and LV and RV function at the time of the second lab draw were also recorded.

Statistics.

Prism 5 software (GraphPad) was used for all statistical analysis. Data are expressed as Mean±SE. A two-tail non-parametric Mann Whitney Test was used for comparison of BIN1 between the control and ARVC groups. For comparison of BIN1 between heart failure patients and healthy controls, a two-tail student's t-test was used with Welch's correction for significant different variances from the two groups. To test for correlations between BIN1 and baseline continuous variables, Spearman analyses were performed. Non-parametric Receiver-Operator Curve (ROC) analyses was used to determine the sensitivity and specificity of BIN1 values to diagnose patients with severe baseline disease and to test for prediction of future arrhythmia events. For comparison of serial BIN1 levels within the same patients, a paired two-tail student's t-test was performed.

Results

Patient Characteristics and Baseline BIN1 Levels.

There were no statistically significant differences between the 24 ARVC patients and 48 controls with respect to age, gender, or BMI (Table 1).

TABLE 1

Baseline Characteristics of ARVC Patients and Controls

| Characteristics | ARVC Patients (n = 24) | Controls (n = 48) | P Value |
|---|---|---|---|
| BIN1 | | | |
| Mean ± SD | 37.1 ± 10 | 60 ± 10 | <0.05 |
| Median | 17 | 27 | |
| Age (years) | 43 ± 15* | 47 +/− 13 | 0.470 |
| Gender | | | |
| Male | 13 | 26 | |
| Female | 11 | 22 | |
| Body Mass Index (BMI) | 25.4 ± 5.9* | 23.6+/1 | 0.200 |
| History | | | |
| Family History Positive Arrhythmias | 8 (33%) | | |
| History of any sustained ventricular | 16 (70%) | | |
| Average length of ICD follow up (years) | 4.4 ± 4.3* | | |
| ICD placed | 23 (96%) | | |
| Primary prevention | 13 (57%) | | |
| Secondary prevention | 10 (43%) | | |
| Heart Failure | | | |
| NYHA class II or greater | 7 (30%) | | |
| NYHA class III or IV | 4 (18%) | | |
| Moderate to severe RV dysfunction | 4 (18%) | | |

*Mean ± SD

Of the 24 ARVC patients, 21 met at least two major criteria and 3 patients met one major and two minor criteria for diagnosis. Eight (33%) had a confirmed family history of ARVC. At the baseline blood draw, 16 (70%) had at least one ventricular arrhythmia event, 7 (30%) were NYHA class II or greater and 4 (18%) were NYHA class III or IV. Four patients (18%) had moderate to severe RV dysfunction. Twenty-three of the 24 patients had ICDs, with an average length of follow up after ICD placement of 4.4±4.3 years to the time of the initial blood draw. Of the patients with ICDs, 13 (57%) were placed for primary prevention and 10 (43%) were placed for secondary prevention.

Plasma BIN1 did not significantly correlate with age, sex or BMI in the ARVC or control populations. In patients with ARVC, BIN1 was not associated with renal function (Table 2). The mean plasma BIN1 level in the ARVC population was 37±1 with a median value of 17, as compared to controls with a mean of 60±10 and a median of 27 (p<0.05) (Table 1).

Cross-Sectional Analysis of BIN1.

Within the ARVC population, measured BIN1 against the absence (NYHA class I) or presence (NYHA class II-IV) of symptomatic heart failure was explored. In ARVC patients with symptomatic heart failure, the mean BIN1 level was 15±7 (n=7), whereas in ARVC patients without clinical heart failure the mean BIN1 level was 60±17 (n=15), (p<0.05). Results are shown in FIG. 8.

Figure 8:
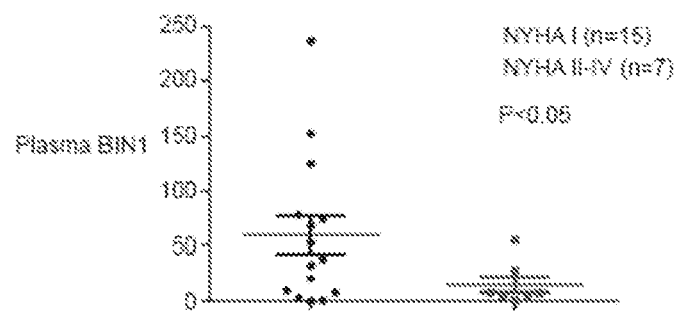
FIG. 8 shows that plasma BIN1 is lower in arrhythmogenic right ventricular cardiomyopathy (ARVC) patients with heart failure.

FIG. 8. Plasma BIN1 is lower in ARVC with HF. Plasma BIN1 (mean±SE) is significantly lower in ARVC patients with symptomatic heart failure (15±7, NYHA N=7, plotted on the right), as compared to ARVC patients without heart failure (60±17, NYHA I, n=15, plotted on the left). P<0.05. (Plasma BIN1 is expressed as percent of BIN1 in plasma pooled from three healthy 25 year old males.)

Spearman analyses were then performed to assess for correlation of plasma BIN1 with baseline continuous clinical variables (Table 2).

TABLE 2

BIN1 Correlation with Baseline Characteristics in ARVC Patients and Controls

| Continuous Variables | Spearman's Rho | P Value |
|---|---|---|
| Number of ventricular arrhythmias to plasma draw | −0.590 | <0.005 |
| Ventricular arrhythmia rate to plasma draw (events/yr.) | −0.460 | <0.05 |
| Length of diagnosis | −0.090 | 0.702 |
| ARVC | | |
| BMI | 0.050 | 0.702 |
| Age | −0.250 | 0.249 |
| GFR | 0.079 | 0.781 |
| Controls | | |
| BMI | 0.019 | 0.902 |
| Age | −0.138 | 0.350 |

* BMI = Body mass index (kg/m$^2$), GFR = Glomerular filtration rate

Plasma BIN1 levels inversely correlated with number of accumulated ventricular arrhythmia events (Rho of −0.60, p<0.01), as well as rate of ventricular arrhythmia events (Rho of −0.46, p<0.05) up to the point of the first plasma measurement (Table 2). For patients with multiple samples, the first sample was used in this analysis. Plasma BIN1 did not significantly correlate with length of ICD follow up.

Figure 9:
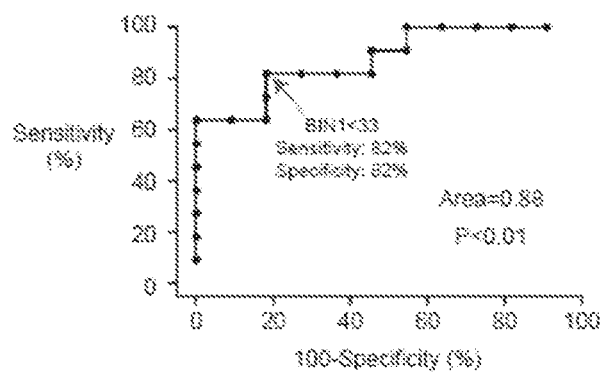
FIG. 9 illustrates that plasma BIN1 predicts severe heart disease (heart failure and/or ventricular arrhythmia) in ARVC patients.

To assess the ability of plasma BIN1 to distinguish between patients with severe and mild ARVC, a Receiver-Operator-Curve analysis was performed (FIG. 9). Severe ARVC was defined as either NYHA class III/IV heart failure, or >1 ventricular arrhythmia event. At a cutoff value of less than 33, plasma BIN1 had an 82% sensitivity and an 82% specificity for predicting NYHA class III/IV heart failure status or >1 ventricular arrhythmia event (ROC AUC of 0.88±0.07). Thus low plasma BIN 1 correlates with the occurrence of severe ARVC.

FIG. 9. Plasma BIN1 predicts disease severity. The Receiver-Operator-Curve analysis indicates that low plasma BIN1 predicts severe ARVC defined as either NYHA class III/IV or >1 ventricular arrhythmias. Plasma BIN1<33 (indicated by the arrow) had an 82% sensitivity and an 82% specificity for predicting patients with NYHA class III/IV heart failure or >1 ventricular arrhythmia event (ROC AUC of 0.88, SE+/−0.07, P<0.01).

Analysis of Plasma BIN1 as a Predictor of Future Arrhythmia Events.

Mean follow up after initial blood draw in the ARVC cohort was 3.3±1.7 yrs. BIN1<30 predicted a high future arrhythmia rate (>0.5/year, FIG. 10) with a sensitivity of 83%, specificity of 88% and an accuracy of 85% (ROC AUC of 0.89±0.09). Given the observed correlation of BIN1 with baseline heart failure and the known increased risk of arrhythmias in patients with heart failure, a stratified analysis was performed according to heart failure status at baseline. In patients with mild heart failure symptoms at baseline (NYHA class I or II, n=20), BIN 1<30 predicted future arrhythmia event rate with a sensitivity of 83%, specificity of 80% and an accuracy of 82% (ROC AUC of 0.82±0.14). In asymptomatic patients (NYHA class I, n=17) at baseline, a BIN1<30 predicted a future high arrhythmia event rate with a sensitivity of 82%, specificity 67% and an accuracy of 79% (ROC AUC of 0.76±0.21). NYHA class II or greater heart failure at baseline alone conferred an unadjusted relative risk of 3.61 (95% CI 1.25-10.37, p<0.05) for high future arrhythmia events.

Figure 10:
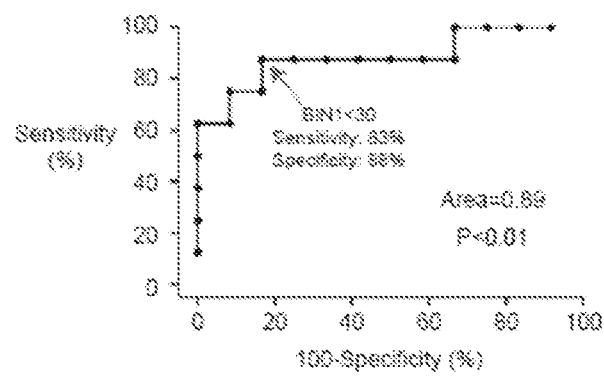
FIG. 10 shows that plasma BIN1 predicts future ventricular arrhythmias.

FIG. 10. Plasma BIN1 predicts future ventricular arrhythmias. The Receiver-Operator-Curve analysis indicates that low plasma BIN1 predicts high future ventricular arrhythmias. Plasma BIN1<30 (indicated by the arrow) predicted a high future arrhythmia rate (>0.5/year) with a sensitivity of 83%, specificity of 88% and an accuracy of 85% (ROC AUC of 0.89, SE+/−0.09, P<0.01).

BIN1 in ARVC Patients with Serial Blood Draws.

Figure 11:
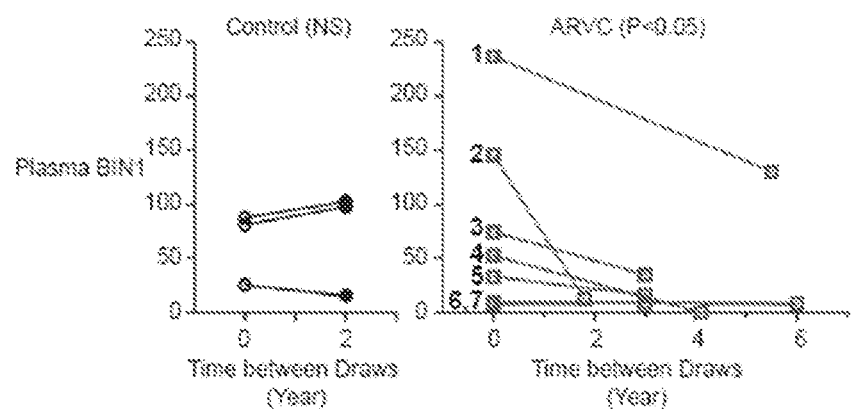
FIG. 11 illustrates that plasma BIN1 decreases with ARVC progression.

Serial blood samples were available in seven ARVC patients and three controls (FIG. 11). Overall, BIN1 values decreased in patients with progressive ARVC. Patient 1 developed new RV dysfunction and had her first episode of VF. Patient 2 developed worsening RV dysfunction and had multiple VF events. Patient 3 had a continued high arrhythmia burden (3.8 events/year) and developed new RV dysfunction. At the time of the initial blood draw, patient 4 did not meet criteria for ARVC, however during follow up the patient developed new T wave inversion in ECG leads V1-V3 and an epsilon wave in V1, palpitations with a high non-sustained VT burden on Holter monitor. She has since had an ICD placed for confirmed ARVC but has not had sustained VT or VF, heart failure, or ventricular dysfunction. Patient 5 had a decrease in LV function from 70% to 49% and the progression from mild to moderate RV dysfunction. Patient 6 had mild RV dysfunction at baseline, but developed moderate RV dysfunction and 5 separate ventricular arrhythmia events. Patient 7 developed mild RV dysfunction during follow up and has had high ventricular arrhythmia rate (2.1 events/year). In sum, patients with clinical progression had marked decreases in their plasma BIN1 levels (decrease of 63%, p<0.05). In contrast, in serial samples from the three healthy controls (FIG. 11), there was no significant change in BIN1 levels over a two year interval.

FIG. 11. Plasma BIN1 decreases with ARVC progression. Serial plasma BIN1 values are shown in controls (circles, n=3) and in ARVC patients (squares, n=7). The plasma BIN1 remained similar in healthy controls (mean±SE from 65±20 to 72±28, NS) while experienced a significant reduction (63% decrease) in ARVC patients during disease progression (mean±SE from 80±32 to 30±17, p<0.05). BIN1 values for ARVC patients were as follows (first draw, second draw): patient 1 (237, 130), patient 2 (145, 130), patient 3 (74, 35), patient 4 (52, <5), patient 5 (33, 16), patient 6 (10, 8), patient 7 (8, 9). (Plasma BIN1 is expressed as percent of BIN1 in plasma pooled from three healthy 25 year old males.)

What is claimed is:

1. A method for assessing for presence of non-acute heart failure in a human subject at risk for heart failure, the method comprising:
    measuring a cardiac BIN1 protein level in a blood, serum or plasma sample obtained from the subject, wherein the measuring is performed by contacting the blood, serum or plasma sample with an anti-cardiac BIN1 antibody;
    comparing the cardiac BIN1 protein level to a normal cardiac BIN1 protein level; and
    assessing the presence of non-acute heart failure in the subject when the cardiac BIN1 protein level is significantly decreased compared to the normal BIN1 protein level, wherein the normal cardiac BIN1 level is obtained from assaying cardiac BIN1 protein in a blood, serum or plasma sample obtained from a healthy human.

2. The method of claim 1, wherein the method further comprises determining a cardiac functional classification of the subject, wherein the cardiac BIN1 protein level is correlated with the cardiac functional classification.

3. The method of claim 1, comprising measuring the cardiac BIN1 protein level in the blood sample.

4. The method of claim 1, comprising measuring the cardiac BIN1 protein level in the serum sample.

5. The method of claim 1, comprising measuring the cardiac BIN1 protein level in the plasma sample.

6. A method of predicting a risk of poor cardiac outcome in a human subject at risk for non-acute heart failure, the method comprising:
    measuring a cardiac BIN1 protein level in a blood, serum or plasma sample obtained from the subject wherein the measuring is performed by contacting the blood, serum or plasma sample with an anti-cardiac BIN1 antibody;
    comparing the cardiac BIN1 protein level to a normal cardiac BIN1 protein level; and
    predicting an increased risk of poor outcome when cardiac BIN1 protein level in the blood, serum or plasma sample is significantly decreased compared to the normal cardiac BIN1 protein level,
    wherein the normal cardiac BIN1 level is obtained from assaying cardiac BIN1 protein in a blood, serum or plasma sample obtained from a healthy human.

7. The method of claim 6, wherein increased risk of a poor outcome comprises increased risk of non-acute heart failure.

8. The method of claim 2, wherein the determining a cardiac functional classification of the subject comprises:
    classifying the subject into a higher cardiac functional class when the cardiac BIN1 protein level is within a first range of 60% to 45% of the normal cardiac BIN1 protein level, or
    classifying the subject into a lower cardiac functional class when the cardiac BIN1 protein level is within a second range of 40% to 0% of the normal cardiac BIN1 protein level.

9. The method of claim 8, wherein the higher cardiac functional class is New York Heart Association (NYHA) Class 1 or Class 2 and the lower cardiac functional class is NYHA Class 3 or Class 4.

10. A method of predicting a risk of cardiac mortality in a human patient diagnosed with chronic heart failure, the method comprising:

measuring a cardiac BIN1 protein level in a blood, serum or plasma sample obtained from the patient wherein the measuring is performed by contacting the blood, serum or plasma sample with an anti-cardiac BIN1 antibody;

comparing the cardiac BIN1 protein level to a normal cardiac BIN1 protein level; and predicting an increased risk of cardiac mortality when the cardiac BIN1 protein level in the blood, serum or plasma sample is significantly decreased compared to the normal cardiac BIN1 protein level, wherein the normal cardiac BIN1 level is obtained from assaying cardiac BIN1 protein in a blood, serum or plasma sample obtained from a chronic heart failure human patient.

* * * * *